US008657870B2

(12) United States Patent
Turovskiy et al.

(10) Patent No.: US 8,657,870 B2
(45) Date of Patent: Feb. 25, 2014

(54) IMPLANT DELIVERY APPARATUS AND METHODS WITH ELECTROLYTIC RELEASE

(75) Inventors: Roman Turovskiy, San Francisco, CA (US); Thuan Ngo, Milpitas, CA (US); Matthew L Davis, Danville, CA (US)

(73) Assignee: Biosensors International Group, Ltd., Hamilton (BM)

( * ) Notice: Subject to any disclaimer, the term of this patent is extended or adjusted under 35 U.S.C. 154(b) by 830 days.

(21) Appl. No.: 12/492,770

(22) Filed: Jun. 26, 2009

(65) Prior Publication Data

US 2010/0331948 A1    Dec. 30, 2010

(51) Int. Cl.
*A61F 2/06* (2013.01)

(52) U.S. Cl.
USPC ........................................ 623/1.12; 623/1.11

(58) Field of Classification Search
USPC ....................................................... 623/1.12
See application file for complete search history.

(56) References Cited

U.S. PATENT DOCUMENTS

| | | |
|---|---|---|
| 4,503,569 A | 3/1985 | Dotter |
| 4,512,338 A | 4/1985 | Balko et al. |
| 4,553,545 A | 11/1985 | Maass et al. |
| 4,562,596 A | 1/1986 | Kornberg |
| 4,580,568 A | 4/1986 | Gianturco |
| 4,655,771 A | 4/1987 | Wallsten |
| 4,665,918 A | 5/1987 | Garza et al. |
| 4,732,152 A | 3/1988 | Wallsten et al. |
| 4,733,665 A | 3/1988 | Palmaz |
| 4,762,128 A | 8/1988 | Rosenbluth |
| 4,768,507 A | 9/1988 | Fischell et al. |
| 4,771,773 A | 9/1988 | Kropf |
| 4,776,337 A | 10/1988 | Palmaz |
| 4,827,941 A | 5/1989 | Taylor et al. |
| 4,830,003 A | 5/1989 | Wolff et al. |
| 4,848,343 A | 7/1989 | Wallsten et al. |
| 4,875,480 A | 10/1989 | Imbert |
| 4,878,906 A | 11/1989 | Lindemann et al. |
| 4,893,623 A | 1/1990 | Rosenbluth |
| 4,913,141 A | 4/1990 | Hillstead |
| 4,950,227 A | 8/1990 | Savin et al. |
| 4,954,126 A | 9/1990 | Wallsten |
| 4,969,890 A | 11/1990 | Sugita et al. |
| 4,990,151 A | 2/1991 | Wallsten |
| 4,990,155 A | 2/1991 | Wilkoff |

(Continued)

FOREIGN PATENT DOCUMENTS

| | | |
|---|---|---|
| DE | 4420142 | 12/1995 |
| EP | 0667 132 | 8/1995 |

(Continued)

OTHER PUBLICATIONS

International Search Report, dated Mar. 29, 2011, from International Patent Application No. PCT/US2010/039041, 6 pages.

(Continued)

*Primary Examiner* — Thomas J Sweet
*Assistant Examiner* — Brian Dukert
(74) *Attorney, Agent, or Firm* — Kilpatrick Townsend & Stockton LLP

(57) ABSTRACT

Implant release apparatus includes a connector connecting a lead having an electrolytically erodible portion and a restraint that restrains the implant. In one embodiment, the connector can include or comprise a nonconductive member.

16 Claims, 24 Drawing Sheets

(56) References Cited

U.S. PATENT DOCUMENTS

| | | |
|---|---|---|
| 4,998,539 A | 3/1991 | Delsanti |
| 5,019,085 A | 5/1991 | Hillstead |
| 5,019,090 A | 5/1991 | Pinchuk |
| 5,026,377 A | 6/1991 | Burton et al. |
| 5,035,706 A | 7/1991 | Giantureo et al. |
| 5,061,275 A | 10/1991 | Wallsten et al. |
| 5,064,435 A | 11/1991 | Porter |
| 5,067,957 A | 11/1991 | Jervis |
| 5,071,407 A | 12/1991 | Termin et al. |
| 5,078,736 A | 1/1992 | Behl |
| 5,089,006 A | 2/1992 | Stiles |
| 5,092,877 A | 3/1992 | Pinchuk |
| 5,102,417 A | 4/1992 | Palmaz |
| 5,108,407 A | 4/1992 | Geremia et al. |
| 5,108,416 A | 4/1992 | Ryan et al. |
| 5,122,136 A | 6/1992 | Guglielmi et al. |
| 5,147,370 A | 9/1992 | McNamara et al. |
| 5,158,548 A | 10/1992 | Lau et al. |
| 5,160,341 A | 11/1992 | Brenneman et al. |
| 5,161,534 A | 11/1992 | Berthiaume |
| 5,171,262 A | 12/1992 | MacGregor |
| 5,180,367 A | 1/1993 | Kontos et al. |
| 5,192,297 A | 3/1993 | Hull |
| 5,197,978 A | 3/1993 | Hess |
| 5,201,757 A | 4/1993 | Heyn et al. |
| 5,221,261 A | 6/1993 | Termin et al. |
| 5,242,399 A | 9/1993 | Lau et al. |
| 5,242,452 A | 9/1993 | Inoue |
| 5,263,964 A | 11/1993 | Purdy |
| 5,266,073 A | 11/1993 | Wall |
| 5,290,305 A | 3/1994 | Inoue |
| 5,306,294 A | 4/1994 | Winston et al. |
| 5,320,635 A | 6/1994 | Smith |
| 5,334,210 A | 8/1994 | Gianturco |
| 5,354,295 A | 10/1994 | Guglielmi et al. |
| 5,360,401 A | 11/1994 | Turnland et al. |
| 5,372,600 A | 12/1994 | Beyar et al. |
| 5,382,259 A | 1/1995 | Phelps et al. |
| 5,405,378 A | 4/1995 | Strecker |
| 5,407,432 A | 4/1995 | Solar |
| 5,415,664 A | 5/1995 | Pinchuk |
| 5,423,829 A | 6/1995 | Pham et al. |
| 5,433,723 A | 7/1995 | Lindenberg et al. |
| 5,443,477 A | 8/1995 | Marin et al. |
| 5,445,646 A | 8/1995 | Euteneuer et al. |
| 5,476,505 A | 12/1995 | Limon |
| 5,484,444 A | 1/1996 | Braunschweiler et al. |
| 5,486,195 A | 1/1996 | Myers et al. |
| 5,507,771 A | 4/1996 | Gianturco |
| 5,522,836 A | 6/1996 | Palermo |
| 5,522,883 A | 6/1996 | Slater et al. |
| 5,534,007 A | 7/1996 | St. Germain et al. |
| 5,540,680 A | 7/1996 | Guglielmi et al. |
| 5,554,181 A | 9/1996 | Das |
| 5,562,697 A | 10/1996 | Christiansen |
| 5,569,245 A | 10/1996 | Guglielmi et al. |
| 5,571,135 A | 11/1996 | Fraser et al. |
| 5,578,074 A | 11/1996 | Mirigian |
| 5,591,196 A | 1/1997 | Marin et al. |
| 5,601,600 A | 2/1997 | Ton |
| 5,607,463 A | 3/1997 | Schwartz et al. |
| 5,618,300 A | 4/1997 | Marin et al. |
| 5,634,928 A | 6/1997 | Fischell et al. |
| 5,639,274 A | 6/1997 | Fischell et al. |
| 5,643,254 A | 7/1997 | Scheldrup et al. |
| 5,653,748 A | 8/1997 | Strecker |
| 5,683,451 A | 11/1997 | Lenker et al. |
| 5,690,643 A | 11/1997 | Wijay |
| 5,690,644 A | 11/1997 | Yurek et al. |
| 5,702,364 A | 12/1997 | Euteneuer et al. |
| 5,702,418 A | 12/1997 | Ravenscroft |
| 5,716,393 A | 2/1998 | Lindenberg et al. |
| 5,725,549 A | 3/1998 | Lam |
| 5,725,551 A | 3/1998 | Myers et al. |
| 5,733,267 A | 3/1998 | Del Toro |
| 5,733,325 A | 3/1998 | Robinson et al. |
| 5,772,609 A | 6/1998 | Nguyen et al. |
| 5,772,668 A | 6/1998 | Summers et al. |
| 5,772,669 A | 6/1998 | Vrba |
| 5,776,141 A | 7/1998 | Klein et al. |
| 5,776,142 A | 7/1998 | Gunderson |
| 5,782,838 A | 7/1998 | Beyar et al. |
| 5,788,707 A | 8/1998 | Del Toro et al. |
| 5,797,857 A | 8/1998 | Obitsu |
| 5,797,952 A | 8/1998 | Klein |
| 5,800,455 A | 9/1998 | Palermo et al. |
| 5,800,517 A | 9/1998 | Anderson et al. |
| 5,807,398 A | 9/1998 | Shaknovich |
| 5,810,837 A | 9/1998 | Hofmann et al. |
| 5,817,101 A | 10/1998 | Fiedler |
| 5,824,041 A | 10/1998 | Lenker et al. |
| 5,824,053 A | 10/1998 | Khosravi et al. |
| 5,824,054 A | 10/1998 | Khosravi et al. |
| 5,824,058 A | 10/1998 | Ravenscroft et al. |
| 5,834,036 A | 11/1998 | Ueno |
| 5,843,090 A | 12/1998 | Schuetz |
| 5,851,206 A | 12/1998 | Guglielmi et al. |
| 5,855,578 A | 1/1999 | Guglielmi et al. |
| 5,860,999 A | 1/1999 | Schnepp-Pesch et al. |
| 5,873,907 A | 2/1999 | Frantzen |
| 5,891,128 A | 4/1999 | Gia et al. |
| 5,919,187 A | 7/1999 | Guglielmi et al. |
| 5,919,204 A | 7/1999 | Lukic et al. |
| 5,919,225 A | 7/1999 | Lau et al. |
| 5,920,975 A | 7/1999 | Morales |
| 5,941,888 A | 8/1999 | Wallace et al. |
| 5,944,726 A | 8/1999 | Blaeser et al. |
| 5,948,017 A | 9/1999 | Taheri |
| 5,957,930 A | 9/1999 | Vrba |
| 5,968,052 A | 10/1999 | Sullivan, III et al. |
| 5,980,485 A | 11/1999 | Grantz et al. |
| 5,980,514 A | 11/1999 | Kupiecki et al. |
| 5,980,530 A | 11/1999 | Willard et al. |
| 5,980,532 A | 11/1999 | Wang |
| 5,980,552 A | 11/1999 | Pinchasik et al. |
| 5,984,929 A | 11/1999 | Bashiri et al. |
| 5,989,242 A | 11/1999 | Saadat et al. |
| 5,989,280 A | 11/1999 | Euteneuer et al. |
| 6,004,328 A | 12/1999 | Solar |
| 6,015,429 A | 1/2000 | Lau et al. |
| 6,017,365 A | 1/2000 | Von Oepen |
| 6,019,737 A | 2/2000 | Murata |
| 6,019,779 A | 2/2000 | Thorud et al. |
| 6,019,785 A | 2/2000 | Strecker |
| 6,027,516 A | 2/2000 | Kolobow et al. |
| 6,027,520 A | 2/2000 | Tsugita et al. |
| 6,042,588 A | 3/2000 | Munsinger et al. |
| 6,042,589 A | 3/2000 | Marianne |
| 6,042,605 A | 3/2000 | Martin et al. |
| 6,048,360 A | 4/2000 | Khosravi et al. |
| 6,053,940 A | 4/2000 | Wijay |
| 6,056,759 A | 5/2000 | Fiedler |
| 6,059,779 A | 5/2000 | Mills |
| 6,059,813 A | 5/2000 | Vrba et al. |
| 6,063,101 A | 5/2000 | Jacobsen et al. |
| 6,063,104 A | 5/2000 | Villar et al. |
| 6,068,634 A | 5/2000 | Lorentzen Cornelius et al. |
| 6,068,644 A | 5/2000 | Lulo et al. |
| 6,071,286 A | 6/2000 | Mawad |
| 6,077,297 A | 6/2000 | Robinson et al. |
| 6,093,194 A | 7/2000 | Mikus et al. |
| 6,096,034 A | 8/2000 | Kupiecki et al. |
| 6,096,045 A | 8/2000 | Del Toro et al. |
| 6,102,942 A | 8/2000 | Ahari |
| 6,113,608 A | 9/2000 | Monroe et al. |
| 6,117,140 A | 9/2000 | Munsinger |
| 6,120,522 A | 9/2000 | Vrba et al. |
| 6,123,714 A | 9/2000 | Gia et al. |
| 6,123,720 A | 9/2000 | Anderson et al. |
| 6,126,685 A | 10/2000 | Lenker et al. |
| 6,139,524 A | 10/2000 | Killion |
| 6,139,564 A | 10/2000 | Teoh |
| 6,139,755 A | 10/2000 | Marte et al. |
| 6,156,061 A | 12/2000 | Wallace et al. |

(56) References Cited

U.S. PATENT DOCUMENTS

| | | | |
|---|---|---|---|
| 6,156,062 A | 12/2000 | McGuinness |
| 6,159,237 A | 12/2000 | Alt et al. |
| 6,161,029 A | 12/2000 | Spreigl et al. |
| 6,165,178 A | 12/2000 | Bashiri et al. |
| 6,168,579 B1 | 1/2001 | Tsugita |
| 6,168,592 B1 | 1/2001 | Kupiecki et al. |
| 6,168,616 B1 | 1/2001 | Brown, III |
| 6,168,618 B1 | 1/2001 | Frantzen |
| 6,174,327 B1 | 1/2001 | Mertens et al. |
| 6,183,481 B1 | 2/2001 | Lee et al. |
| 6,183,505 B1 | 2/2001 | Mohn, Jr. et al. |
| 6,193,708 B1 | 2/2001 | Ken et al. |
| 6,200,305 B1 | 3/2001 | Berthiaume et al. |
| 6,203,550 B1 | 3/2001 | Olson |
| 6,206,888 B1 | 3/2001 | Bicek et al. |
| 6,214,036 B1 | 4/2001 | Letendre et al. |
| 6,221,081 B1 | 4/2001 | Mikus et al. |
| 6,221,097 B1 | 4/2001 | Wang et al. |
| 6,228,110 B1 | 5/2001 | Munsinger |
| 6,231,564 B1 | 5/2001 | Gambale |
| 6,231,597 B1 | 5/2001 | Deem et al. |
| 6,231,598 B1 | 5/2001 | Berry et al. |
| 6,238,410 B1 | 5/2001 | Vrba et al. |
| 6,238,430 B1 | 5/2001 | Klumb et al. |
| 6,241,758 B1 | 6/2001 | Cox |
| 6,245,097 B1 | 6/2001 | Inoue |
| 6,248,122 B1 | 6/2001 | Klumb et al. |
| 6,254,609 B1 | 7/2001 | Vrba et al. |
| 6,254,611 B1 | 7/2001 | Vrba |
| 6,254,628 B1 | 7/2001 | Wallace et al. |
| 6,264,671 B1 | 7/2001 | Stack et al. |
| 6,264,683 B1 | 7/2001 | Stack et al. |
| 6,267,783 B1 | 7/2001 | Letendre et al. |
| 6,270,504 B1 | 8/2001 | Lorentzen Cornelius et al. |
| 6,273,881 B1 | 8/2001 | Kiemeneij |
| 6,280,465 B1 | 8/2001 | Cryer |
| 6,287,331 B1 | 9/2001 | Heath |
| 6,302,893 B1 | 10/2001 | Limon et al. |
| 6,306,141 B1 | 10/2001 | Jervis |
| 6,306,162 B1 | 10/2001 | Patel |
| 6,319,275 B1 | 11/2001 | Lashinski et al. |
| 6,342,066 B1 | 1/2002 | Toro et al. |
| 6,344,041 B1 | 2/2002 | Kupiecki et al. |
| 6,346,118 B1 | 2/2002 | Baker et al. |
| 6,350,277 B1 | 2/2002 | Kocur |
| 6,350,278 B1 | 2/2002 | Lenker et al. |
| 6,361,637 B2 | 3/2002 | Martin et al. |
| 6,368,344 B1 | 4/2002 | Fitz |
| 6,371,962 B1 | 4/2002 | Ellis et al. |
| 6,371,979 B1 | 4/2002 | Beyar et al. |
| 6,375,660 B1 | 4/2002 | Fischell et al. |
| 6,379,365 B1 | 4/2002 | Diaz |
| 6,380,457 B1 | 4/2002 | Yurek et al. |
| 6,383,174 B1 | 5/2002 | Eder |
| 6,387,118 B1 | 5/2002 | Hanson |
| 6,391,050 B1 | 5/2002 | Broome |
| 6,391,051 B2 | 5/2002 | Sullivan, III et al. |
| 6,395,017 B1 | 5/2002 | Dwyer et al. |
| 6,409,750 B1 | 6/2002 | Hyodoh et al. |
| 6,409,752 B1 | 6/2002 | Boatman et al. |
| 6,413,269 B1 | 7/2002 | Bui et al. |
| 6,416,536 B1 | 7/2002 | Yee |
| 6,416,545 B1 | 7/2002 | Mikus et al. |
| 6,423,090 B1 | 7/2002 | Hancock |
| 6,425,898 B1 | 7/2002 | Wilson et al. |
| 6,425,914 B1 | 7/2002 | Wallace et al. |
| 6,425,915 B1 | 7/2002 | Khosravi et al. |
| 6,428,489 B1 | 8/2002 | Jacobsen et al. |
| 6,428,566 B1 | 8/2002 | Holt |
| 6,432,080 B2 | 8/2002 | Pederson, Jr. et al. |
| 6,432,129 B2 | 8/2002 | DiCaprio |
| 6,447,540 B1 | 9/2002 | Fontaine et al. |
| 6,448,700 B1 | 9/2002 | Gupta et al. |
| 6,451,025 B1 | 9/2002 | Jervis |
| 6,451,052 B1 | 9/2002 | Burmeister et al. |
| 6,454,795 B1 | 9/2002 | Chuter |
| 6,458,092 B1 | 10/2002 | Gambale et al. |
| 6,468,266 B1 | 10/2002 | Bashiri et al. |
| 6,468,298 B1 | 10/2002 | Pelton |
| 6,468,301 B1 | 10/2002 | Amplatz et al. |
| 6,482,227 B1 | 11/2002 | Solovay |
| 6,485,515 B2 | 11/2002 | Strecker |
| 6,488,700 B2 | 12/2002 | Klumb et al. |
| 6,514,285 B1 | 2/2003 | Pinchasik |
| 6,517,548 B2 | 2/2003 | Lorentzen Cornelius et al. |
| 6,517,569 B2 | 2/2003 | Mikus et al. |
| 6,520,986 B2 | 2/2003 | Martin et al. |
| 6,530,947 B1 | 3/2003 | Euteneuer et al. |
| 6,533,805 B1 | 3/2003 | Jervis |
| 6,533,807 B2 | 3/2003 | Wolinsky et al. |
| 6,537,295 B2 | 3/2003 | Petersen |
| 6,558,415 B2 | 5/2003 | Thompson |
| 6,562,063 B1 | 5/2003 | Euteneuer et al. |
| 6,562,064 B1 | 5/2003 | deBeer |
| 6,579,297 B2 | 6/2003 | Bicek et al. |
| 6,579,308 B1 | 6/2003 | Jansen et al. |
| 6,582,460 B1 | 6/2003 | Cryer |
| 6,602,226 B1 | 8/2003 | Smith et al. |
| 6,602,272 B2 | 8/2003 | Boylan et al. |
| 6,607,539 B1 | 8/2003 | Hayashi et al. |
| 6,607,551 B1 | 8/2003 | Sullivan et al. |
| 6,613,079 B1 | 9/2003 | Wolinsky et al. |
| 6,623,518 B2 | 9/2003 | Thompson et al. |
| 6,626,938 B1 | 9/2003 | Butaric et al. |
| 6,629,981 B2 | 10/2003 | Bui et al. |
| 6,645,237 B2 | 11/2003 | Klumb et al. |
| 6,645,238 B2 | 11/2003 | Smith |
| 6,656,212 B2 | 12/2003 | Ravenscroft et al. |
| 6,660,031 B2 | 12/2003 | Tran et al. |
| 6,660,032 B2 | 12/2003 | Klumb et al. |
| 6,663,660 B2 | 12/2003 | Dusbabek et al. |
| 6,663,664 B1 | 12/2003 | Pacetti |
| 6,666,881 B1 | 12/2003 | Richter et al. |
| 6,669,719 B2 | 12/2003 | Wallace et al. |
| 6,676,666 B2 | 1/2004 | Vrba et al. |
| 6,679,910 B1 | 1/2004 | Granada |
| 6,689,120 B1 | 2/2004 | Gerdts |
| 6,692,521 B2 | 2/2004 | Pinchasik |
| 6,699,274 B2 | 3/2004 | Stinson |
| 6,702,843 B1 | 3/2004 | Brown et al. |
| 6,702,846 B2 | 3/2004 | Mikus et al. |
| 6,709,425 B2 | 3/2004 | Gambale et al. |
| 6,716,238 B2 | 4/2004 | Elliott |
| 6,726,714 B2 | 4/2004 | DiCaprio et al. |
| 6,733,519 B2 | 5/2004 | Lashinski et al. |
| 6,736,839 B2 | 5/2004 | Cummings |
| 6,802,858 B2 | 10/2004 | Gambale et al. |
| 6,814,746 B2 | 11/2004 | Thompson et al. |
| 6,818,014 B2 | 11/2004 | Brown et al. |
| 6,821,291 B2 | 11/2004 | Bolea et al. |
| 6,830,575 B2 | 12/2004 | Stenzel et al. |
| 6,833,002 B2 | 12/2004 | Stack et al. |
| 6,833,003 B2 | 12/2004 | Jones et al. |
| 6,843,802 B1 | 1/2005 | Villalobos et al. |
| 6,858,034 B1 | 2/2005 | Hijlkema et al. |
| 6,860,899 B1 | 3/2005 | Rivelli, Jr. |
| 6,875,212 B2 | 4/2005 | Shaolian et al. |
| 6,878,161 B2 | 4/2005 | Lenker |
| 6,936,058 B2 | 8/2005 | Forde et al. |
| 6,936,065 B2 | 8/2005 | Khan et al. |
| 6,989,024 B2 | 1/2006 | Hebert et al. |
| 7,004,964 B2 | 2/2006 | Thompson et al. |
| 7,011,673 B2 | 3/2006 | Fischell et al. |
| 7,022,132 B2 | 4/2006 | Kocur |
| 7,074,236 B2 | 7/2006 | Rabkin et al. |
| 7,127,789 B2 | 10/2006 | Stinson |
| 7,172,620 B2 | 2/2007 | Gilson |
| 7,300,460 B2 | 11/2007 | Levine et al. |
| 7,393,357 B2 | 7/2008 | Stelter et al. |
| 7,399,311 B2 | 7/2008 | Bertolino et al. |
| 7,771,463 B2 | 8/2010 | Ton et al. |
| 2001/0034548 A1 | 10/2001 | Vrba et al. |
| 2001/0047185 A1 | 11/2001 | Satz |
| 2001/0049547 A1 | 12/2001 | Moore |

(56) References Cited

U.S. PATENT DOCUMENTS

| | | |
|---|---|---|
| 2001/0049550 A1 | 12/2001 | Martin et al. |
| 2002/0002397 A1 | 1/2002 | Martin et al. |
| 2002/0032431 A1 | 3/2002 | Kiemeneij |
| 2002/0035393 A1 | 3/2002 | Lashinski et al. |
| 2002/0040236 A1 | 4/2002 | Lau et al. |
| 2002/0045928 A1 | 4/2002 | Boekstegers |
| 2002/0045930 A1 | 4/2002 | Burg et al. |
| 2002/0049490 A1 | 4/2002 | Pollock et al. |
| 2002/0068966 A1 | 6/2002 | Holman et al. |
| 2002/0072729 A1 | 6/2002 | Hoste et al. |
| 2002/0077693 A1 | 6/2002 | Barclay et al. |
| 2002/0095147 A1 | 7/2002 | Shadduck |
| 2002/0095168 A1 | 7/2002 | Griego et al. |
| 2002/0099433 A1 | 7/2002 | Fischell et al. |
| 2002/0120322 A1 | 8/2002 | Thompson et al. |
| 2002/0120323 A1 | 8/2002 | Thompson et al. |
| 2002/0120324 A1 | 8/2002 | Holman et al. |
| 2002/0138129 A1 | 9/2002 | Armstrong et al. |
| 2002/0147491 A1 | 10/2002 | Khan et al. |
| 2002/0161342 A1 | 10/2002 | Rivelli et al. |
| 2002/0165600 A1 | 11/2002 | Banas et al. |
| 2002/0169494 A1 | 11/2002 | Mertens et al. |
| 2002/0188341 A1 | 12/2002 | Elliott et al. |
| 2003/0014103 A1 | 1/2003 | Inoue |
| 2003/0018319 A1 | 1/2003 | Kiemeneij |
| 2003/0036768 A1 | 2/2003 | Hutchins et al. |
| 2003/0040771 A1 | 2/2003 | Hyodoh et al. |
| 2003/0040772 A1 | 2/2003 | Hyodoh et al. |
| 2003/0045923 A1 | 3/2003 | Bashiri |
| 2003/0055377 A1 | 3/2003 | Sirhan et al. |
| 2003/0065375 A1 | 4/2003 | Eskuri |
| 2003/0069521 A1 | 4/2003 | Reynolds et al. |
| 2003/0069522 A1 | 4/2003 | Jacobsen et al. |
| 2003/0100848 A1 | 5/2003 | Gosiengfiao et al. |
| 2003/0105508 A1 | 6/2003 | Johnson et al. |
| 2003/0135266 A1 | 7/2003 | Chew et al. |
| 2003/0144731 A1 | 7/2003 | Wolinsky et al. |
| 2003/0149467 A1 | 8/2003 | Linder et al. |
| 2003/0163156 A1 | 8/2003 | Hebert et al. |
| 2003/0163189 A1 | 8/2003 | Thompson et al. |
| 2004/0002728 A1 | 1/2004 | Speck et al. |
| 2004/0010265 A1 | 1/2004 | Karpiel |
| 2004/0010304 A1 | 1/2004 | Weber et al. |
| 2004/0049547 A1 | 3/2004 | Matthews et al. |
| 2004/0087965 A1 | 5/2004 | Levine et al. |
| 2004/0093063 A1 | 5/2004 | Wright et al. |
| 2004/0097917 A1 | 5/2004 | Keane |
| 2004/0127912 A1 | 7/2004 | Rabkin et al. |
| 2004/0193178 A1 | 9/2004 | Nikolchev |
| 2004/0193179 A1 | 9/2004 | Nikolchev |
| 2004/0193246 A1 | 9/2004 | Ferrera |
| 2004/0220585 A1 | 11/2004 | Nikolchev |
| 2004/0260377 A1 | 12/2004 | Flomenblit et al. |
| 2005/0049592 A1 | 3/2005 | Keith et al. |
| 2005/0049668 A1 | 3/2005 | Jones et al. |
| 2005/0049669 A1 | 3/2005 | Jones et al. |
| 2005/0049670 A1 | 3/2005 | Jones et al. |
| 2005/0080430 A1 | 4/2005 | Wright, Jr. et al. |
| 2005/0096724 A1 | 5/2005 | Stenzel et al. |
| 2005/0096727 A1 | 5/2005 | Allen et al. |
| 2005/0209670 A1 | 9/2005 | George et al. |
| 2005/0209671 A1 | 9/2005 | Ton et al. |
| 2005/0209672 A1 | 9/2005 | George et al. |
| 2005/0209675 A1 | 9/2005 | Ton et al. |
| 2005/0220836 A1 | 10/2005 | Falotico et al. |
| 2005/0246010 A1 | 11/2005 | Alexander et al. |
| 2006/0085057 A1 | 4/2006 | George et al. |
| 2006/0136037 A1 | 6/2006 | DeBeer et al. |
| 2006/0190070 A1 | 8/2006 | Dieck et al. |
| 2006/0247661 A1 | 11/2006 | Richards et al. |
| 2006/0270948 A1 | 11/2006 | Viswanathan et al. |
| 2006/0271097 A1* | 11/2006 | Ramzipoor et al. .......... 606/200 |
| 2006/0276886 A1 | 12/2006 | George et al. |
| 2007/0027522 A1 | 2/2007 | Chang et al. |
| 2007/0043419 A1 | 2/2007 | Nikolchev et al. |
| 2007/0073379 A1 | 3/2007 | Chang et al. |
| 2007/0100414 A1* | 5/2007 | Licata et al. ................. 623/1.11 |
| 2007/0100415 A1 | 5/2007 | Licata |
| 2007/0100416 A1 | 5/2007 | Licata |
| 2007/0100417 A1 | 5/2007 | Licata |
| 2007/0100418 A1 | 5/2007 | Licata |
| 2007/0100419 A1 | 5/2007 | Licata |
| 2007/0100420 A1 | 5/2007 | Kavanagh et al. |
| 2008/0015541 A1 | 1/2008 | Rosenbluth et al. |
| 2008/0071309 A1 | 3/2008 | Mazzocchi et al. |
| 2008/0188921 A1 | 8/2008 | Yamasaki |
| 2008/0221666 A1* | 9/2008 | Licata et al. ................. 623/1.22 |
| 2009/0281611 A1 | 11/2009 | Geroges et al. |

FOREIGN PATENT DOCUMENTS

| | | |
|---|---|---|
| EP | 0 747 021 | 12/1996 |
| EP | 1 157 673 | 11/2001 |
| EP | 1518515 | 3/2005 |
| JP | 2002-538938 | 11/2002 |
| WO | WO 97/12563 | 4/1997 |
| WO | WO 97/48343 | 12/1997 |
| WO | WO 98/23241 | 6/1998 |
| WO | WO 99/04728 | 2/1999 |
| WO | WO 99/08740 | 2/1999 |
| WO | WO 00/18330 | 4/2000 |
| WO | WO 00/56248 | 9/2000 |
| WO | WO 01/78627 | 10/2001 |
| WO | WO 03/073963 | 9/2003 |
| WO | WO 2004/087006 | 10/2004 |
| WO | WO 2005/094727 | 10/2005 |

OTHER PUBLICATIONS

Bonsignore, "A Decade of Evolution in Stent Design" SMST-2003: Proceedings of the International Conference on Shape Memory and Superelastic Technologies, 2004, pp. 519-528.

Definitions of "abut" and "wire"—Random House College Dictionary, 1980, New York, 7 and 510.

Duerig et al., "An overview of superelastic stent design" Min fnvas Ther & Affied Technol. 9(3/4 ):235-246 (2000).

Fischell et al. "A Fixed Guidewire Stent Delivery System Rationale and Design" TCT. Washington. D.C. (Sep. 24, 2002).

Kandzari et al. "Clinical and Angiographic Efficacy of a Self-Expanding Nitinol Stent in Saphenous Vein Graft Atherosclerotic Disease" Am. Heart J 145(5):868-874 (2003).

Poncet, "Nitinol Medical Device Design Considerations" SMST-2000: Proceedings of the International Conference on Shape Memory and Superelastic Technologies, 2001, pp. 441-455.

Rieu et al., "Radial Force of Coronary Stents: A Comparative Analysis" Catheterization and Cardiovascular Interventions 46:380-391 (1999).

Rogers, C. "DES Overview: Agents: release mechanism and stent platform", Brigham and Women's Hospital PowerPoint Presentation (undated), 51 pages total.

Schuessler et al., "Stent Materials and Manufacturing: Requirements and Possibilities/Opportunities," ASM Materials & Processes for Medical Devices, Anaheim, CA. (Sep. 8-10, 2003).

Stoeckel et al., "A Survey of Stent Designs" Min Invas Ther & Allied Technol 11(4):137-147 (2002).

Welt et al. "Coronary Artery Stents: Design and Biologic Considerations" Cardiology Special Edition 9(2) 9-14(2003).

\* cited by examiner

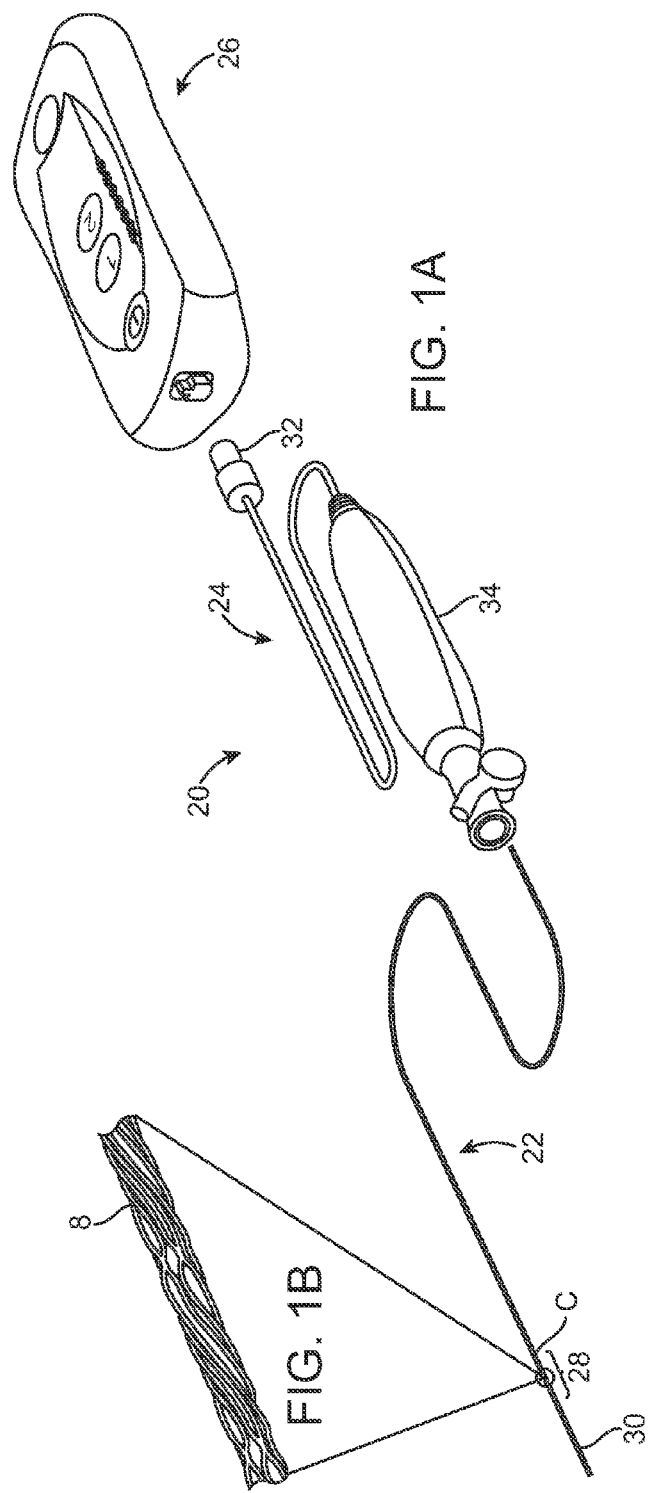
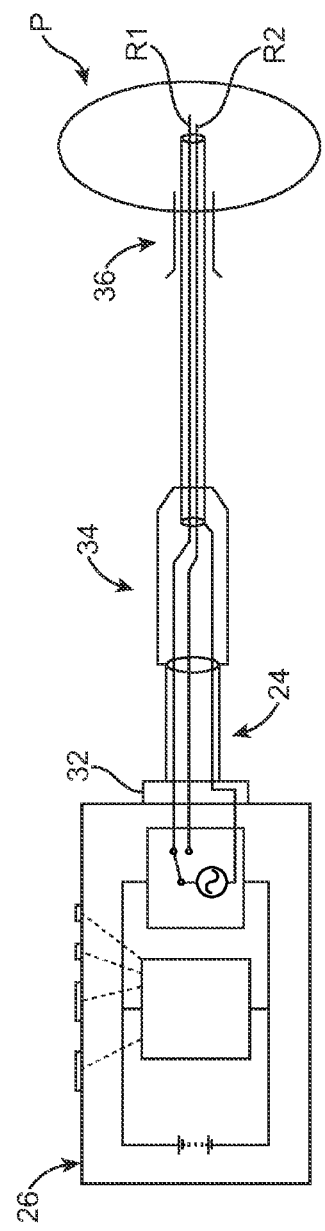
FIG. 1A
FIG. 1B
FIG. 1C

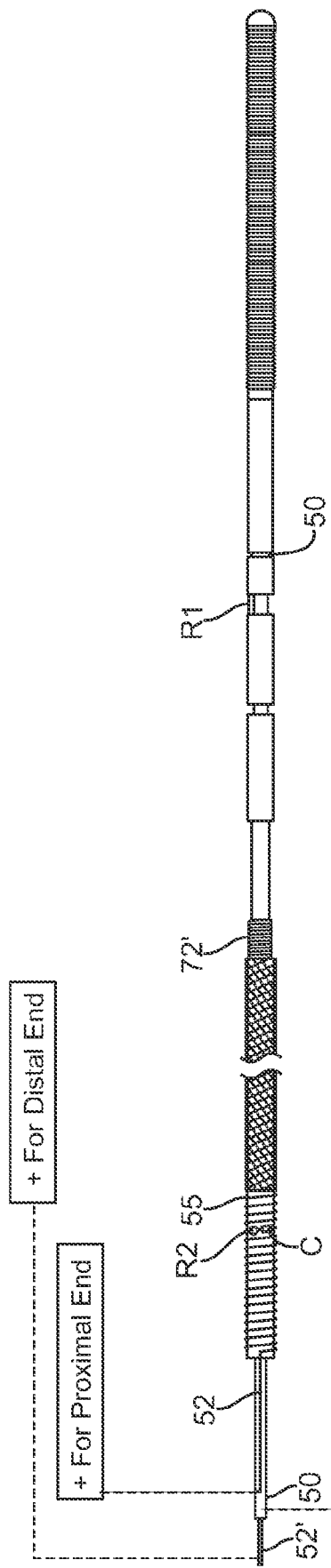
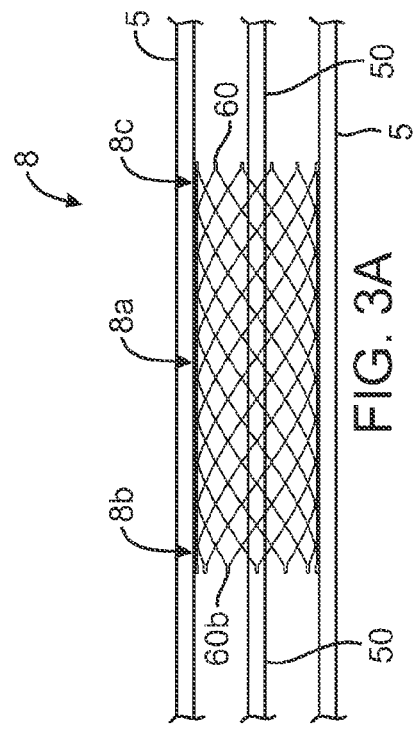

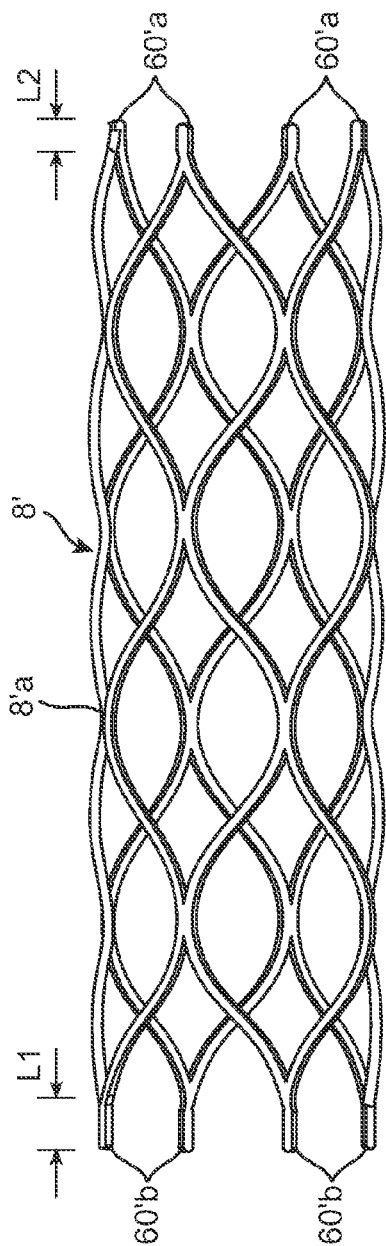
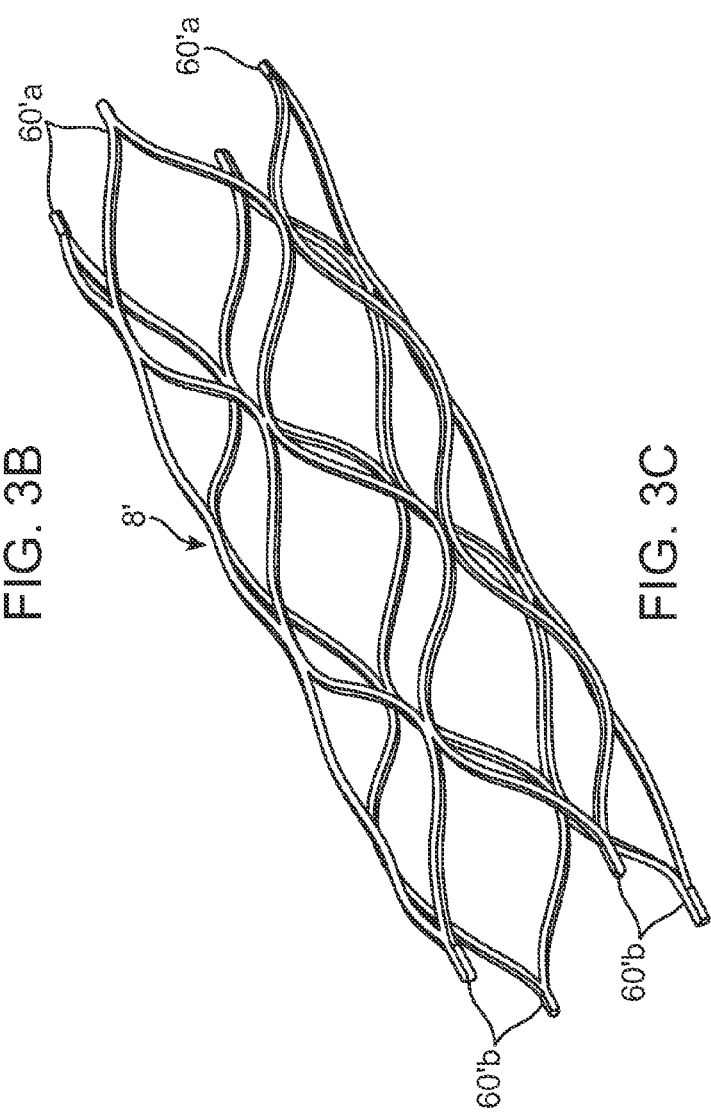
FIG. 3B
FIG. 3C

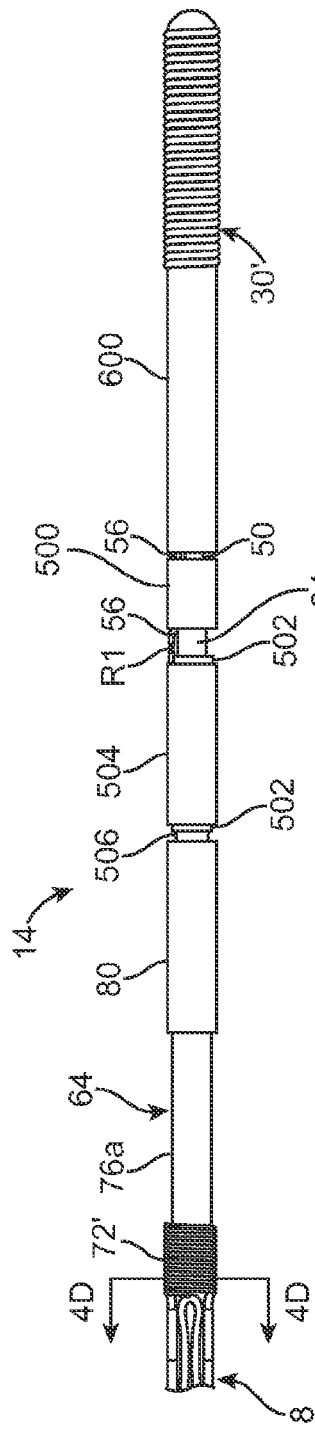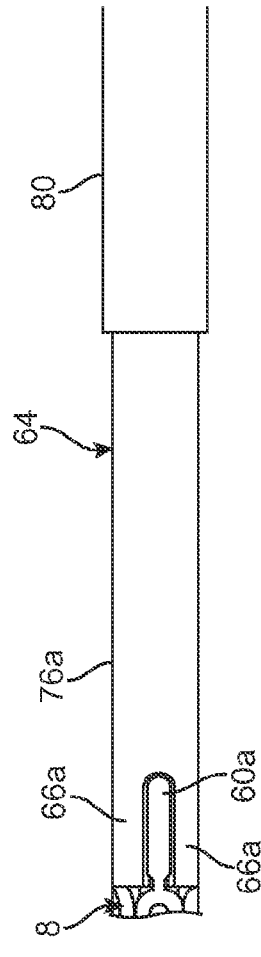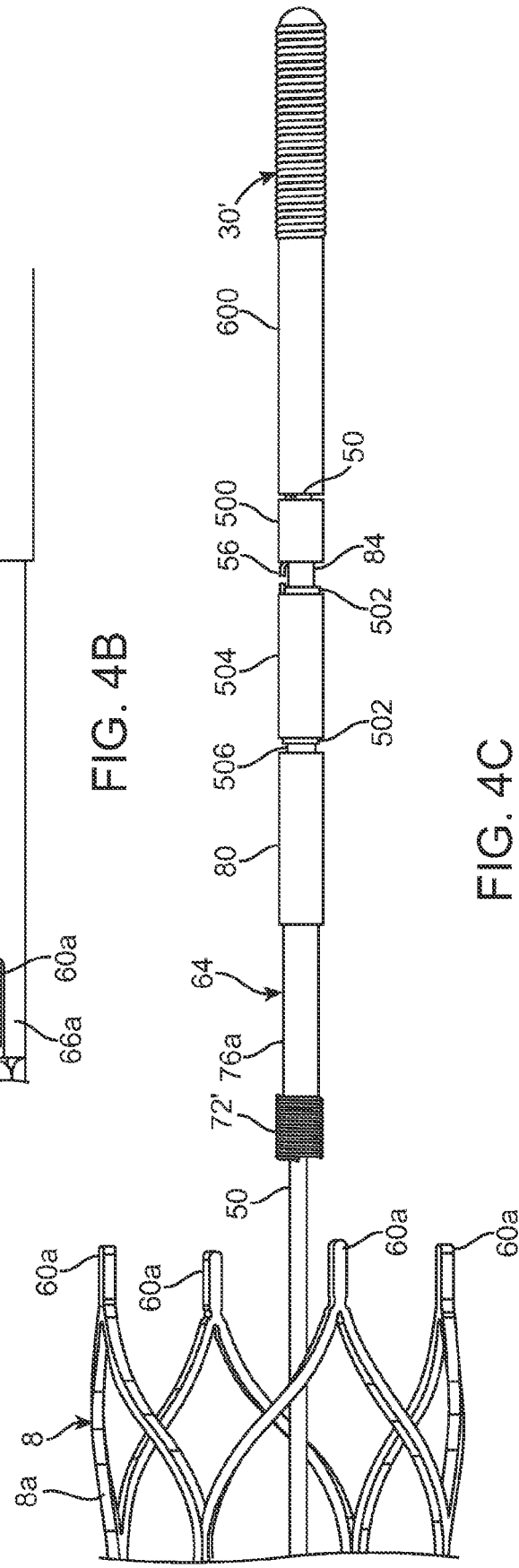

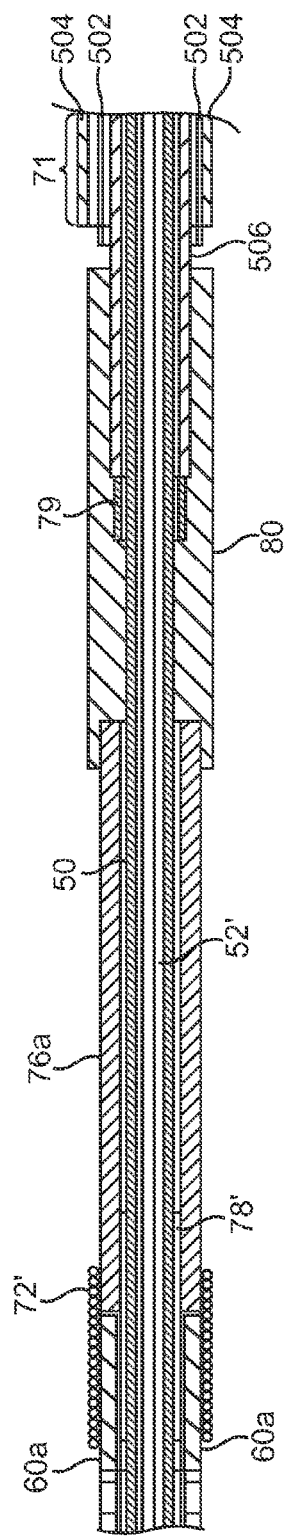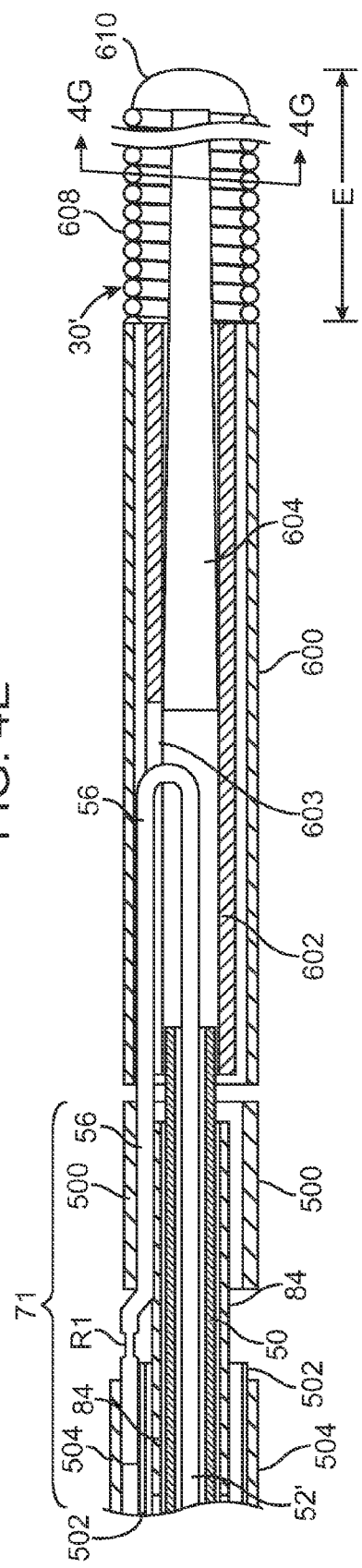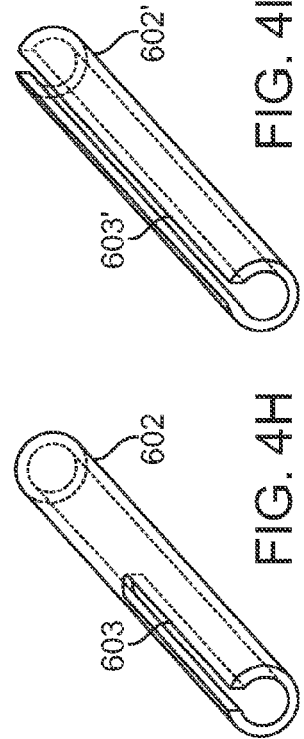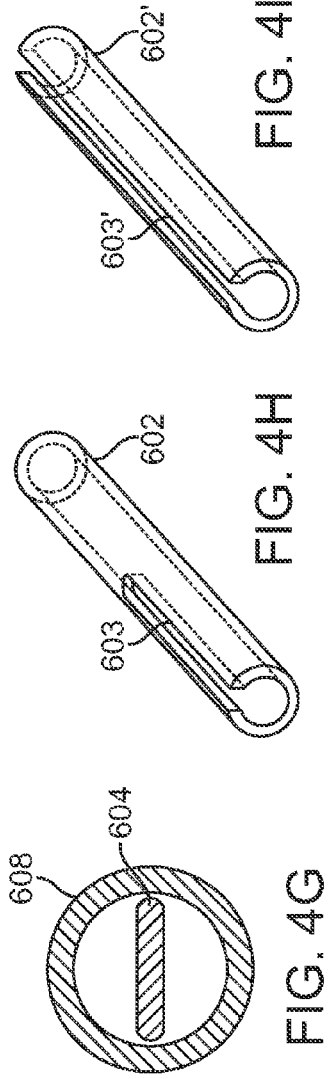

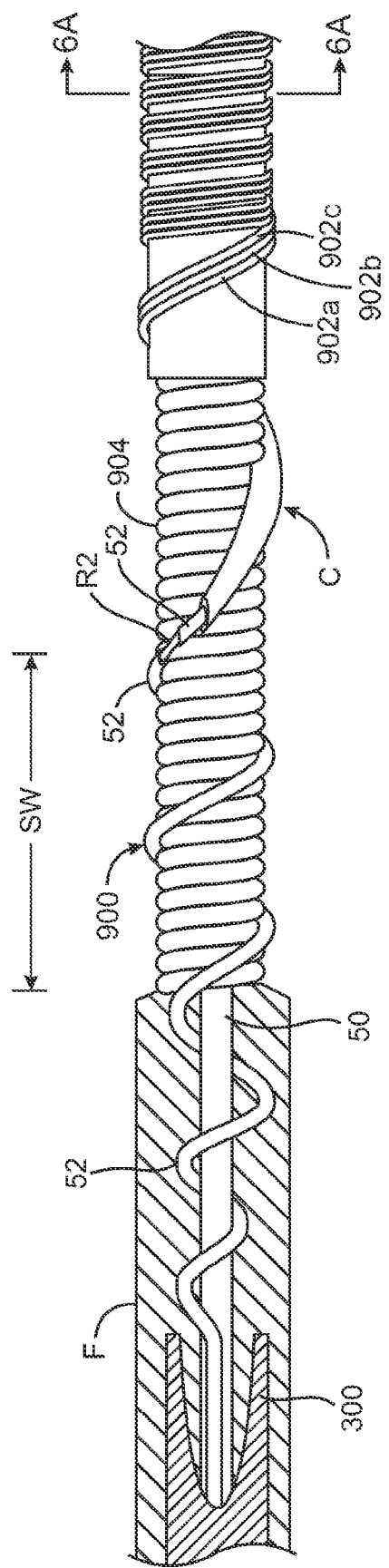

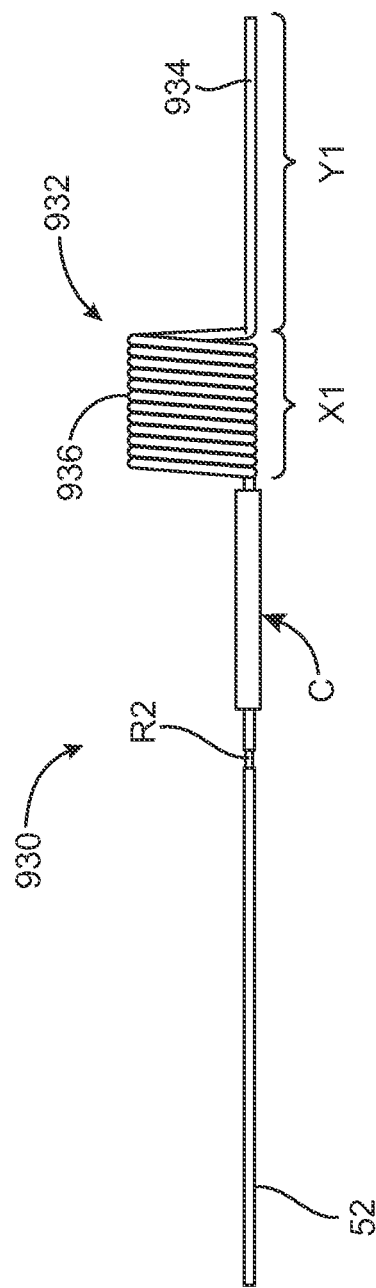

FIG. 16D1

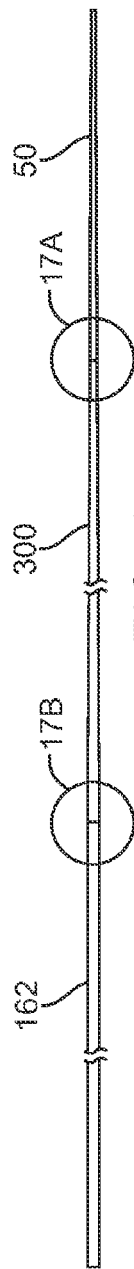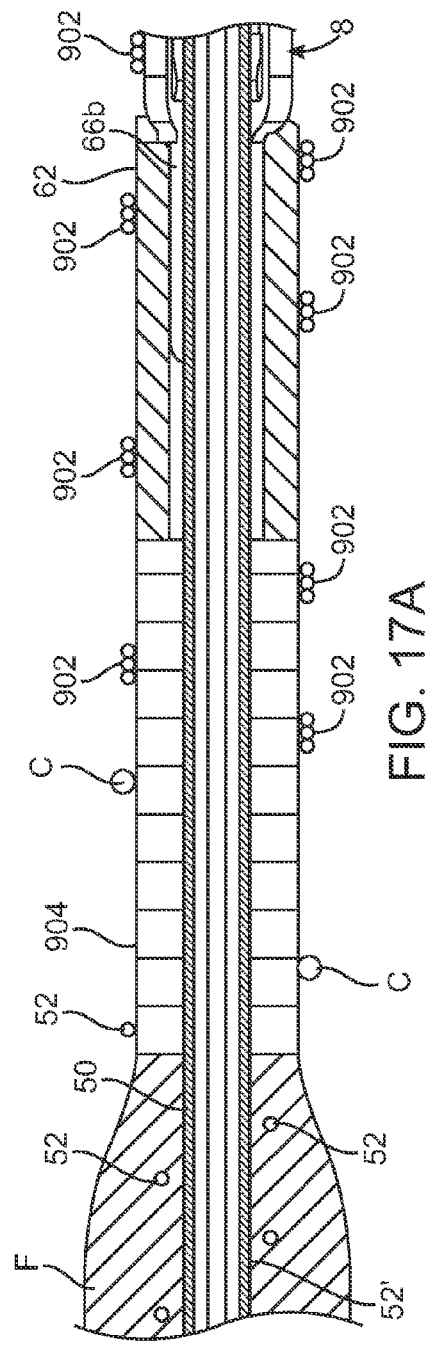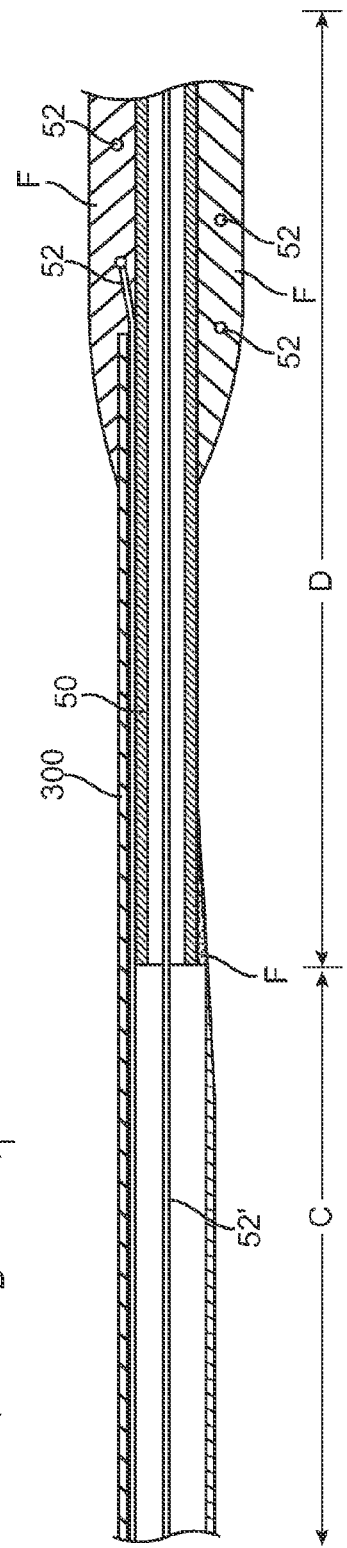
FIG. 17
FIG. 17A
FIG. 17B

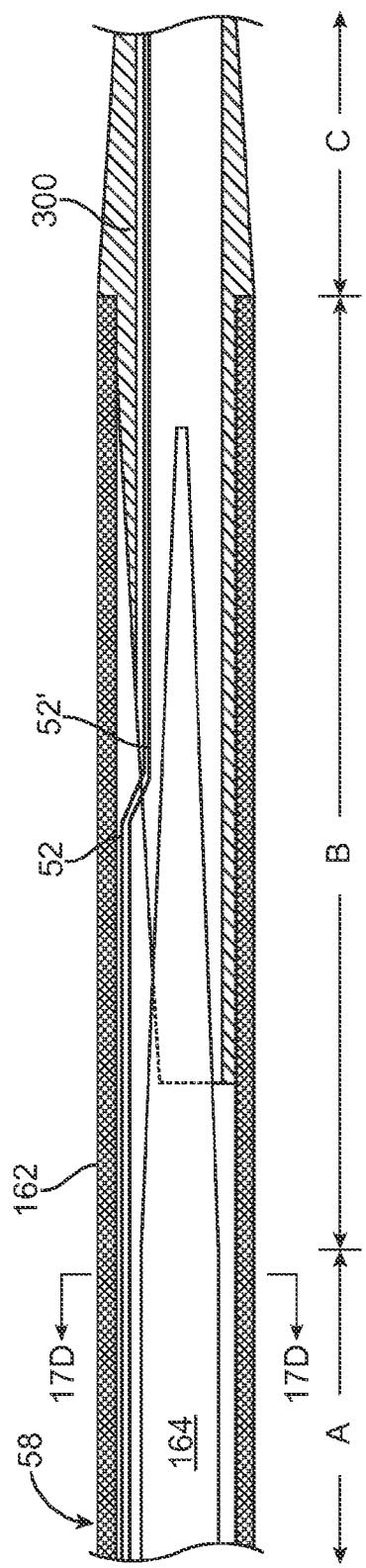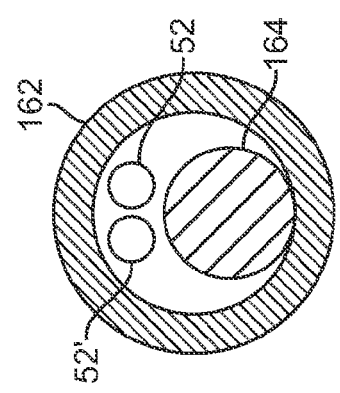

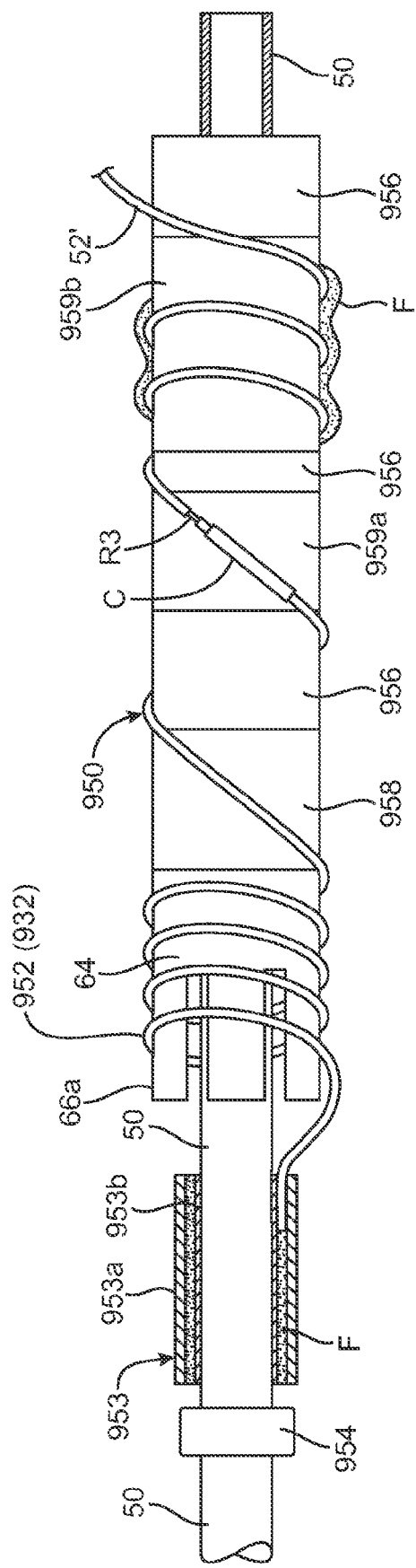

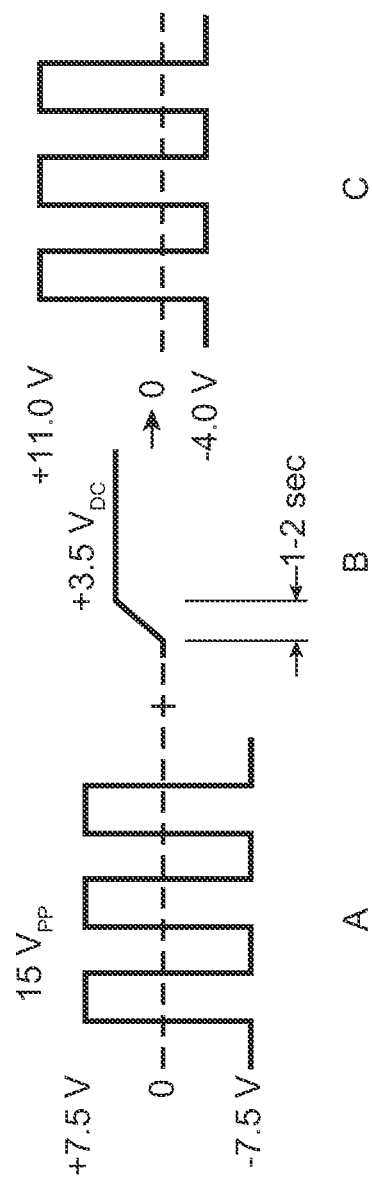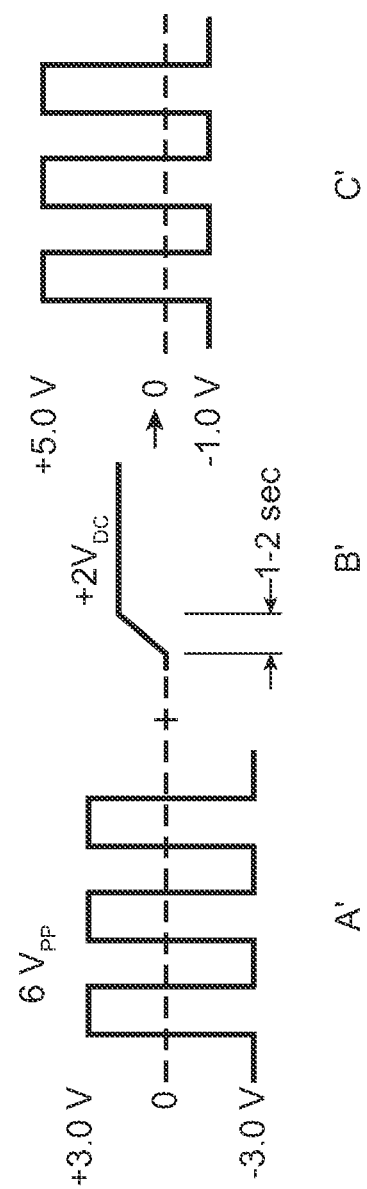

8,657,870 B2

IMPLANT DELIVERY APPARATUS AND METHODS WITH ELECTROLYTIC RELEASE

BACKGROUND OF THE INVENTION

Field of the Invention

The application relates to endoluminal delivery systems and more particularly to electrolytic implant release apparatus.

Implants such as stents and occlusive coils have been used in patients to treat wide variety of abnormalities and/or diseases such as cardiovascular or neurovascular abnormalities. One of the most common "stenting" procedures is carried out in connection with the treatment of atherosclerosis, a disease which results in a narrowing and stenosis of body lumens, such as the coronary arteries. At the site of the narrowing (i.e., the site of a lesion) a balloon is typically dilated in an angioplasty procedure to open the vessel. A stent is placed within the lumen in order to help maintain an open passageway. The stents typically are bare stent or drug eluting stents.

There remain challenges in endoluminal stent delivery through tortuous and/or small vasculature and a need to improve stent delivery apparatus and/or systems.

BRIEF SUMMARY OF THE INVENTION

In one embodiment according to the invention, an implant delivery system comprises an elongated delivery guide having a distal end and a proximal end; a self-expanding implant mounted on the elongated delivery guide, the implant having a distal end and a proximal end; a first restraint releasably coupling one of the implant ends to the delivery guide; a second restraint releasably coupling the other of the implant ends to the delivery guide; an electrical conductor adapted to be coupled to a power supply and having an erodible section; and an electrically nonconductive member connecting the first restraint and the electrical conductor. In this manner, the first restraint and first conductor erodible section can be electrically isolated from one another to prevent undesirable shorting between the restraint and stent without using an insulation tube therebetween and advantageously reduce delivery profile.

In another embodiment according to the invention, an implant delivery system comprises an elongated delivery guide having a distal end and a proximal end; a self-expanding implant mounted on the elongated delivery guide, the implant having a distal end and a proximal end; a first restraint releasably coupling one of the implant ends to the delivery guide; a second restraint releasably coupling the other of the implant ends to the delivery guide; an electrical conductor adapted to be coupled to a power supply and having an erodible section; and a member comprising epoxy connecting the first restraint and the electrical conductor.

In another embodiment according to the invention, an implant delivery system comprises an elongated delivery guide having a distal end and a proximal end; a self-expanding implant mounted on the elongated delivery guide, the implant having a distal end and a proximal end; a first restraint releasably coupling one of the implant ends to the delivery guide; a second restraint releasably coupling the other of the implant ends to the delivery guide; an electrical conductor adapted to be coupled to a power supply and having an erodible section; and a connector connecting the first restraint and the electrical conductor wherein the first restraint and the electrical conductor comprise or are formed from different materials.

The above is a brief description of some deficiencies in the prior art and advantages of the present invention. Other features, advantages, and embodiments of the invention will be apparent to those skilled in the art from the following description and accompanying drawings, wherein, for purposes of illustration only, specific forms of the invention are set forth in detail.

BRIEF DESCRIPTION OF THE DRAWINGS

FIG. 1A is a perspective view of an implant delivery system according to the invention.

FIG. 1B is a perspective view of a portion of the system of FIG. 1A.

FIG. 1C is a schematic view depicting an exemplary embodiment of the electrical hardware of FIG. 3A.

FIG. 2 diagrammatically illustrates one embodiment of a distal end portion of the delivery guide of FIG. 1A a stent loaded thereon in a radially compressed and twisted configuration.

FIG. 3A diagrammatically illustrates the stent of FIG. 2 released from the delivery guide.

FIGS. 3B and 3C are side and perspective views, respectively, of another stent configuration that can be mounted to or carried on the delivery guide of FIG. 2.

FIG. 4A diagrammatically illustrates a distal portion of the embodiment of FIG. 2 showing the distal releasable stent restraint mechanism restraining the stent in a radially compressed and twisted configuration.

FIG. 4B diagrammatically illustrates a section of the portion shown in FIG. 4A with the distal stent restraint removed to show the stent tabs seated in the delivery guide distal stent seat.

FIG. 4C diagrammatically illustrates the section of FIG. 4A in a released state where the distal end of the stent is radially expanded after release.

FIG. 4E is a longitudinal sectional view of a portion of the device shown in FIG. 4A.

FIG. 4F is a longitudinal sectional view of the distal end portion of the device shown in FIG. 4A and illustrating one distal tip embodiment.

FIG. 4G is a sectional view taken along line 4G-4G in FIG. 4F showing the distal tip coil over the double flat corewire.

FIG. 4H is a perspective view of the connector of FIG. 4F.

FIG. 4I is a perspective view of another connector embodiment.

FIG. 5A is a partial sectional view of the portion shown in FIG. 5.

FIG. 14B shows the restraint in the form of a loop and looped around and secured to the delivery guide, and FIG. 14C shows the restraint further wrapped around the stent receiving seat prior to being secured to the delivery guide at a location proximal to the seat.

FIG. 15A illustrates another proximal releasable stent restraint mechanism according to the invention.

FIGS. 16A, 16B, 16C, 16D, 16D1, 16E, 16F, and 16G illustrate a method for loading a stent in the distal section of the delivery guide according to the invention.

FIG. 17 diagrammatically illustrates a delivery guide embodiment without the stent and distal coil tip secured thereto.

FIG. 17A is a sectional view of the delivery guide taken along a first length of the delivery guide extending proximally from the proximal portion of the stent.

FIG. 17B is a sectional view of a portion of the delivery guide proximal to the portion shown in FIG. 17A.

FIG. 17C is a sectional view of a portion of the delivery guide proximal to the portion shown in FIG. 17B.

FIG. 17D is a sectional view taken along line 17D-17D in FIG. 17C.

FIG. 18A is a partial sectional view of the distal releasable stent restraint mechanism of FIG. 18.

FIGS. 21A and 21B illustrate exemplary power profiles for exemplary embodiments of the delivery system.

DETAILED DESCRIPTION OF THE INVENTION

Figure 4D:
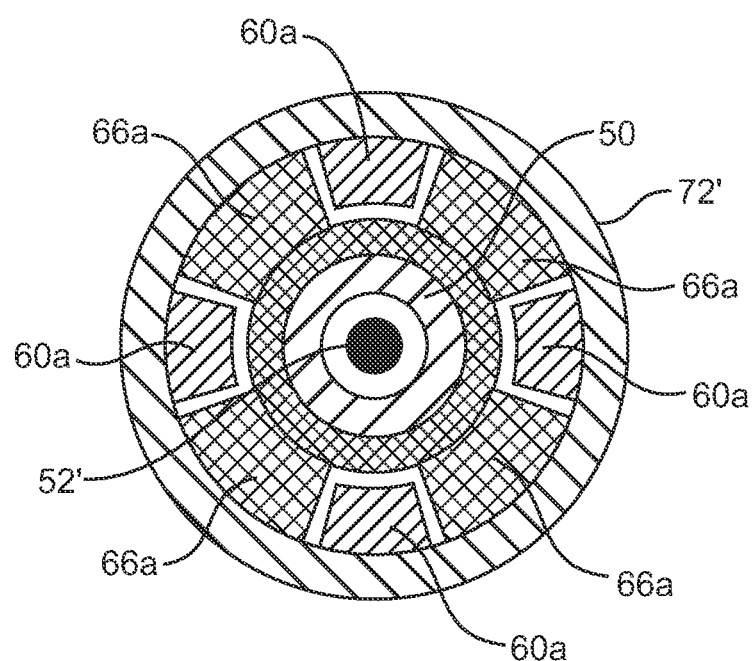
FIG. 4D is sectional view taken along line 4D-4D in FIG. 4A.

The following description will be made with reference to the drawings where when referring to the various figures, it should be understood that like numerals or characters indicate like elements. Further, before the present invention is described, it is to be understood that this invention is not intended to be limited to particular embodiments or examples described, as such may, of course, vary.

The devices and systems described herein can be used for example, in treating a heart by locating and releasing one or more stents within any of the coronary arteries. Stenting can be practiced in conjunction with angioplasty or "direct stenting" can be employed, where the stent can be delivered alone to maintain a body conduit, without balloon angioplasty. However, balloon predilatation and/or postdilatation at the site of the lesion to be treated can be employed. The balloon can be advanced to the site of the lesion prior to advancement of the delivery system or afterwards, in which case the delivery system can be used as a guide for the balloon catheter. Alternatively, the balloon can reside on the delivery system itself.

The system is advantageously sized for use in accordance with a "through-the-lumen," methodology as described in U.S. patent application Ser. No. 10/746,455 "Balloon Catheter Lumen Based Stent Delivery Systems" filed on Dec. 24, 2003, which published as U.S. Patent Application Publication No. 2004/0193179 on Sep. 30, 2004, and its PCT counterpart PCT/US2004/008909 filed on Mar. 23, 2004, the disclosure of each of these references being hereby incorporated by reference herein in its entirety. The delivery guide can be capable of use as a lead guidewire suitable for over-the-wire or Rapid Exchange balloon catheter approaches. Alternatively, it can be substituted for a guidewire within the lumen of a balloon catheter as an intermediate step in an angioplasty procedure. Access to a treatment site is otherwise achieved with a collection of known devices in a manner routine to those with skill in the art.

The delivery guide also can be used in other procedures such as implanting an anchoring stent in a hollow tubular body organ or delivering a device or stent to cage or completely close-off an aneurysm.

In sum, the delivery guide described herein is constructed to function and serve as a guidewire and therefore also can be referred to as a guidewire.

A "stent" as used herein includes any stent, such as coronary artery stents, other vascular prosthesis, or other radially expanding or expandable prosthesis, or scaffold-type implant suitable for the noted treatments and the like. Exemplary structures include wire mesh, ring or lattice structures. A "self-expanding" stent as used herein is a scaffold-type structure (serving any of a number of purposes) that expands from a reduced-diameter configuration (be it circular or otherwise) to an increased-diameter configuration. The mechanism for shape recovery can be elastic or pseudoelastic or driven by a crystalline structure change (as in a Shape Memory Alloy, i.e., SMA). While it is generally desirable to employ an alloy (such as nickel-titanium, or Nitinol alloy) set for use as a superelastic alloy, the material can alternatively employ thermal shape memory properties to drive expansion upon release.

Stents used with the devices, systems and methods described herein can be uniquely suited for a system able to reach small vessels (though use of the subject systems is not so-limited). By "small" vessels, it is meant vessels having an inside diameter from between about 1.5 to 2.75 mm and up to about 3 mm in diameter. These vessels include, but are not limited to, the Posterior Descending Artery (PDA), Obtuse Marginals (OMs) and small diagonals. Conditions such as diffuse stenosis and diabetes produce situations that represent other access and delivery challenges that can be addressed with the devices, systems and methods described herein. Other extended treatment areas addressable with the subject systems include vessel bifurcations, chronic total occlusions (CTOs), and prevention procedures (such as in stenting of vulnerable plaque).

A Drug Eluting Stent (DES) can be used in an application to aid in lessening late lumen loss and/or preventing restenosis. A review of suitable drug coatings and available vendors is presented in "DES Overview: Agents, release mechanism, and stent platform" a presentation by Campbell Rogers, MD incorporated by reference in its entirety. Examples of various therapeutic agents that can be used in or on the subject prosthesis include (but are not limited to) antibiotics, anticoagulants, antifungal agents, anti-inflammatory agents, antineoplastic agents, antithrombotic agents, endothelialization promoting agents, free radical scavengers, immunosuppressive agents, antiproliferative agents, thrombolytic agents, and any combination thereof. The therapeutic agent can be coated onto the implant, mixed with suitable carrier and then coated onto the implant, or (when the implant is made from a polymeric material) dispersed throughout the polymer. The agent can be directly applied to the stent surface(s), or introduced into pockets or an appropriate matrix set over at least an outer portion of the stent. The drug matrix, and/or even the stent itself, can be biodegradable. Several biodegradable matrix options are available though companies such as Biosensors International, Surmodics, Inc. and others. It is also recognized that bare-metal stents can also be employed.

In use, a self-expanding stent will typically be sized so that it is not fully expanded when fully deployed against the wall of a vessel in order to provide a measure of radial force thereto (i.e., the stent will be "oversized" relative to the vessel diameter). In a superelastic NiTi stent adapted for compression to an outer diameter of about 0.014 or about 0.018 inches and expansion to about 3.5 mm, the thickness of the NiTi can be between about 0.002 to about 0.003 inches (0.05-0.08 mm). Such a stent is designed for use in about a 3 mm vessel or other body conduit, thereby providing the desired radial force.

Such a stent can comprise NiTi that is superelastic at or below room temperature (i.e., as in having an Af as low as 0 to −15 degrees C.), or upwards of that, close to human body temperature (i.e., as in having and Af as high as 30 to 35 degrees C.). The stent can be electropolished to improve biocompatibility and corrosion and fatigue resistance. Alternatively, various ternary alloys such as ones including chromium, platinum or other metals—for various reasons—can be employed.

Other materials and material procession approaches can be utilized for the stent as well. In addition to a drug or other coating or partial covering as referenced above, the stent can be coated with gold, palladium and/or platinum or any other biocompatible radiopaque substance to provide improved radiopacity for viewing under medical imaging. As practiced by Implant Sciences, Inc., a base layer of chromium can be desired to enhance adhesion of the more radiopaque metal layer(s). Various platinum or tantalum, etc. markers can additionally or alternatively be employed.

A superelastic nitinol (NiTi) stent for use with the devices, systems and methods described herein can be configured according to the cut pattern as taught in U.S. patent application Ser. No. 11/238,646 (pattern also shown in FIGS. 3A and 3B with a stent tab length variation), which published under U.S. Patent Application Publication No. 2006/0136037 on Jun. 22, 2006, the disclosure of each of these references being hereby incorporated herein by reference in its entirety. Such a design is well suited for use in small vessels. It can be collapsed to an outer diameter of about 0.018 inch (0.46 mm), 0.014 inch (0.36 mm) or even smaller—and expanded to a size (fully unrestrained) between about 1.5 mm (0.059 inch) or 2 mm (0.079 inch) or 3 mm (0.12 inch) and about 3.5 mm (0.14 inch).

For use in twist-down type stent compression with delivery systems as described herein, end tabs or projections are typically provided to mate with complimentary seat features. While straight projections are shown, others can be used as described in U.S. patent application Ser. No. 11/266,587, which published under U.S. Patent Application Publication No. 2006/0111771 on May 25, 2006, and U.S. patent application Ser. No. 11/265,999, which published under U.S. Patent Application Publication No. 2007/0100414 (the disclosure of each of these references being hereby incorporated herein by reference in its entirety). The latter filing also describes in detail a manner of twist-loading stents.

Referring to FIGS. 1A-C, implant delivery system 20 for delivering implants such as stents is shown. Delivery system 20 includes a delivery guide 22, a power adapter 24, and a power supply 26. A distal section 28 of delivery guide 22 carries stent 8 that is releasably secured to delivery guide 22. The delivery guide 22 will typically terminate in an atraumatic coil tip 30. FIG. 1B shows an enlarged stent section 28 where in this example the implant is a stent. As shown, the stent is held in a compressed diameter in-part by virtue of the twist imparted thereto. Restraints holding stent 8 to delivery guide 22 are released through erosion of electrolytically erodible joints by application of voltage via power supply 26 to the joints as will be described in more detail below. A connector "C" having an electrically nonconductive member, which is provided between at least one of the electrolytically erodible joints and a restraint, also will be described in further detail below.

The electrolytic erosion of a bare/exposed metal electrical conductor, which forms the electrolytically erodible joint, is driven by applying voltage to develop a positive charge on the element resulting in a motive force to cause current to flow to a (relatively) negatively charged body (e.g. a neutral pole). Current flows by ion transfer from the section to be eroded to the neutral body through an electrolytic solution. Within a patient, the solution is the patient's blood. Further discussion of electrolytic detachment/release is presented in various patents including U.S. Pat. No. 5,122,136 to Guglielmi; U.S. Pat. No. 6,716,238 to Elliot; U.S. Pat. No. 6,168,592 to Kupiecki, et al.; U.S. Pat. No. 5,873,907 to Frantzen and the multiplicity of continuation, continuations-in-part and divisional applications related to these patents.

Power supply 26 incorporates a circuit board and one or more batteries (e.g., lithium ion "coin" cells or a 9V battery) to provide power to the system's features to selectively drive the erosion so that one electrolytic joint can be eroded first and then the other. The power supply shown is reusable. It will typically be bagged (bag not shown) within an operating room. A disposable power adapter/extension 24 including appropriate connectors 32 and a handle interface 34 can be provided in sterile packaging with the delivery guide 22. Referring to FIG. 1C, a schematic illustration of the electrical hardware shown in FIG. 1A is shown where an introducer catheter 36, the patient's body "P" and electrodes or erodible sections "R1" and "R2."

In support of implant delivery, it is also to be understood that various radiopaque markers or features can be employed in the delivery system to (1) locate implant position and length, (2) indicate device actuation and implant delivery and/or (3) locate the distal end of the delivery guide. As such, platinum (or other radiopaque material) bands, use of such material in constructing various elements of the subject systems, and/or markers (such as tantalum plugs) can be incorporated into delivery guide 22.

In one exemplary embodiment, delivery guide 22 with stent 8 mounted thereon is advantageously sized to match the diameter of a commercially available guidewire. In the most compact variations, the delivery guide loaded with the stent has an effective diameter that can range from 0.014 inch (0.36 mm) up to and including 0.018 inch (0.46 mm). However, the system can even be advantageously practiced at 0.022 inch (0.56 mm) or 0.025 inch (0.64 mm) sizes. Of course, intermediate sized delivery guides can be employed as well, especially for full-custom systems.

In smaller sizes, the system is applicable in "small vessel" cases or applications or treatment. In larger sizes, the system is most applicable to larger, peripheral vessel applications, or other hollow body organs. The latter applications involve a stent emplaced in a region having a diameter from about 3.5 to 13 mm (0.5 inch).

Referring to FIG. 2, one embodiment of a distal end portion of delivery guide 22 is shown diagrammatically with stent 8 loaded and held thereon in a radially compressed and twisted configuration. Distal section 28 of delivery guide 22 (FIG. 1A) carries stent 8, while stent 8 is held in a compressed and twisted configuration over elongated member 50, which can be a tube or hypotube. In the configuration where elongated member 50 is a tube, electrical lead 52' is passed through the tube and lead 52 is extended along the tube after which both are coupled to power supply 26 as will be described in further detail below.

Lead 52 includes an electrolytically erodible section or joint "R2" and is connected to proximal stent restraint 55 through connector C. Proximal stent restraint 55 wraps around a proximal end of stent 8 and holds that proximal end in a radially compressed configuration or diameter.

Lead 52' has a distal portion 56 (FIG. 4F), which includes an electrolytically erodible section or joint "R1" that is operatively coupled to the distal stent restraint 72' as will be described in more detail below. Therefore, lead 52' and distal portion 56 can be formed from the same material or wire. Alternatively, lead 52' and lead distal portion 56 can comprise two of pieces wire such as copper for the lead and stainless steel for the wrap where the pieces are connected (e.g. soldered) together.

In the illustrative embodiment, power input into lead 52' creates a circuit from electrolytically erodible section or joint "R1" to the patient's blood and then back to ground through central tube 50 or other conductive component in delivery guide 22 and then to corewire 164 (see e.g., FIG. 17C). Power input into lead 52 similarly creates a circuit from "R2" to the patient's blood and then back to ground through central tube 50 or other conductive component in delivery guide 22 and then to corewire 164. After electrolytically erodible sections or joints "R1" and "R2" have been eroded stent 8 is fully released so that it can expand against the inner wall of tubular member or organ 5 as shown in FIG. 3A. Tubular member 5 can be, for example, a coronary artery or other vessel in a human patient.

Returning to FIG. 2, leads 52 and 52' can be connected to discrete channels or circuits, for example, in one power supply or two separate power supplies (in combination with a return lead/path as can be provided by electrically conductive components of the delivery system such as central tube 50, tube 300, corewire 164, body tube 162, and connections to the power supply), a specialized catheter, for example, as described in U.S. Pat. No. 6,059,779 to Mills, or an external pad placed upon a patient's body, for example as described in U.S. Pat. No. 6,620,152 to Guglielmi) to provide individual control over corrosion of the wires. Such a setup can be desired in order to first release the distal side of the implant and then release the proximal side.

Further, erosion of the electrolytically erodible joints can be monitored so that when current no longer flows in a given circuit, positive indication is offered that the subject erodible joint has been eroded or released. Another beneficial factor is that by eroding one erodible joint at a time, current can be limited, in contrast to a system in which multiple sections of material would be eroded at once. The current draw necessary to erode the subject electrolytically erodible joints is also minimized by controlling the size of the erodible section.

Leads or electrically conductive wires 52 and 52' are insulated except for electrolytically erodible sections or joints "R1" and "R2," which also may be referred to as sacrificial links. To define the erodible or sacrificial section, nonconductive insulation (e.g., polyimide insulation) or a protective layer of noble (or more noble) metal such as platinum or gold covered other portions of the material is stripped off, removed, or never laid-down in the first place via a masking process at the section. Stainless steel wire will generally be selected for its strength and because it offers corrosion resistance "on the shelf" while being erodible in an electrolytic solution under power. Other material selection and construction options as discussed in the incorporated references are possible as well.

Precisely manufactured electrolytically erodible sections or joints "R1" and "R2" can be produced using a laser to ablate insulation on wire over a selected region. Such an approach is advantageously employed to provide erodible exposed wire section(s) having a length as little as about 0.001 inches long. More typically, the erodible exposed wire sections have a length that ranges from about 0.001 to about 0.010, preferably between about 0.002 and about 0.004 inches on a wire having a diameter between about 0.00075 and about 0.002 inches. Insulation thickness can be as little as about 0.0004 to about 0.001 inches, especially when an intermediate protective polymer layer is employed in the latch assembly as described in further detail herein. Its thickness can fall outside this range as well—as can other dimensions not indicated as critical herein.

Referring to FIG. 3A, stent 8 has a near or proximal end 8b, a far or distal end 8c, a main body or support structure 8a extending between the near and far ends. Stent 8 also includes distal stent end projections or tabs 60a and proximal stent end projections or tabs 60b. The restraints described above restrain distal stent projections or tabs 60a in guide member seat 64 (see e.g., FIG. 4B) and proximal projections or tabs 60b in seat 62 (see e.g., FIG. 6A) to hold the stent in a twisted and radially compressed configuration.

Stent 8 comprises a plurality of axially/horizontally adjacent struts or arms/legs that define a lattice of closed cells as described in U.S. patent application Ser. No. 11/238,636 as referenced above. Such closed-cell designs facilitate twist-down of the stent because the otherwise free ends of an open ended cell (or successive ring) design have a tendency to radially lift-off in a radial direction due to complex stress distributions. Whereas coil stents are twisted in bulk, their component parts are typically largely placed in tension. With the lattice-type stent designs, the overall tubular body is subject to torque-based loading.

The projections advantageously have a length that allow for efficient transition or transfer twisting load to the stent while occupying minimal space. Though usable with the devices, systems and methods described herein, projections longer than about one cell's length can have a tendency to wrap or twist about the delivery device body in attempted use. For a stent and delivery system adapted to present an 0.014 crossing profile, the tabs can be approximately 0.020 inches in length and between about 0.002 and about 0.005 inches wide.

Referring to FIGS. 3B and 3C, another stent embodiment is shown and generally designated with reference numeral 8'. Stent 8' has distal tabs 60'a and proximal tabs 60'b that extend from the closed cell stent body 8a' and that are generally parallel to the longitudinal axis of the stent when in an unconstrained, relaxed state. In this embodiment, proximal stent tabs 60'b are longer than distal stent tabs 60'a measured in the aforementioned longitudinal axis. This configuration facilitates quick release of the distal end of the stent, while allowing the proximal end to be securely held in the event that stent relocation is desired. In one embodiment, proximal stent tabs are twice as long as stent tabs 60'a measured in the aforementioned longitudinal axis. This stent configuration is disclosed in U.S. patent application Ser. No. 11/957,211, entitled Stent Systems, filed Dec. 14, 2007 and published as U.S. Patent Application Publication No. 2008/0221666, the disclosure of each of these references is incorporated by reference herein in its entirety.

This different length tabs tab feature is not related to improvements for compaction, but rather to facilitate stent release from the delivery guide. As shortened tabs (approximately one-half the length of the other, or about 0.010 inches long) can be advantageous when employed with an un-twisting style of release mechanism, such as distal latch mechanism 71 as shown in FIGS. 4A and C. It can be especially useful with fixed stent restraining band 72' because less length for 60a will be needed to slide out of the seat in order to achieve (at least partial) stent release.

As referenced above, outside of the stent tab lengths, the stent design can correspond to that disclosed in the above-referenced U.S. patent application Ser. No. 11/238,646, which published under U.S. Patent Application Publication No. 2006/0136037 on Jun. 22, 2006, the disclosure of each of these references being hereby incorporated by reference herein in its entirety. (See, e.g., FIGS. 2A-B, 5A-C, 6A-B, 7A-B, 8A-B and their associated texts, as well as paragraphs 58-64, 90-95, 101-107).

Referring to FIG. 4A-4F, the distal releasable stent restraint mechanism will be described. In the illustrative embodiment, coil 72' covers axially extending distal tabs or projections 60a, which extend from stent body 8a of stent 8, as shown in FIGS. 4A-C. Stent 8 has a closed cell construction as shown, for example, in FIGS. 3A-3C. Such a closed cell construction is a non-coil type construction where the stent struts or wire form closed cells. Restraint 72' keeps tabs 60a seated in seat 64 (see e.g., FIG. 4F, which is a transverse sectional view taken through restraint 72') and keeps the tabs from radially expanding, and thus the stent in a compressed state for low profile delivery. When stent 8' is used, restraint 72' covers distal tabs or projections 60'a.

In the illustrative embodiment, the overall release mechanism comprises distal latch assembly 71 and a key assembly. Distal latch assembly 71 includes tubes 504, 502, 500, and 84 and wire 56 with erodible or sacrificial portion R1. The distal key assembly includes members 64, 72', 78', and 79, latch mount 506, and connector tube 80.

Referring to FIGS. 4E and 4F, the distal key and latch assembly will be described in further detail. Distal coil band 72', which can be made out of 0.0012 inch wire, is laser welded to distal fingers 66a of seat 64, which is soldered to tubular connector tube 80. Tubular connector 80 is soldered to tubular latch mount 506. In this manner, tube or sleeve 80 connects seat body 76a to hub or tubular member 506, which extends into tubular member 502, which is surrounded by tubular member 504. Tubular stabilizer 78', which can be, for example NiCo, is slidably positioned around central tube 50 and slidably positioned within the inner perimeter of tabs 60a and seat fingers 66a such that it can freely float or slide. Stabilizer band 78' provides support for tabs 60a and friction reduction to facilitate stent deployment. Tubular blocker 79 is soldered to central tube or twist mandrel 50 and is sized to prevent latch mount 506 and all elements fixedly secured to latch mount 506 (i.e., members 64, 72', and 80 and distal latch assembly 71) from moving proximally. Tubes 502 and 504 are not secured to the twist mandrel 50 so they can rotate as the stent untwists.

Distal latch assembly 71 is epoxied to latch mount 506 by epoxying tube 502 over latch mount 506. Tube 502 is bonded to tube 504 and at the same time wire 56 is bonded between tubes 502 and 504. For example, wire 56 can be epoxied to tubes 502 and 504 to secure or bond wire 56 to tubes 502 and 504. Tube 502 is bonded over latch mount 506 and the distal end of insulative tube or sleeve 84 is bonded to the twist mandrel 50.

Coil band 72', distal key 64, tube 80, tubular latch mount 506, tubular blocker 79, and central tube or twist mandrel 50 can comprise stainless steel to provide and electrically conductive pathway for ground. An additional layer of insulative material such as insulative tube or sleeve 84 can be provided between wire 56 and erodible section "R1" and central tube 50 to provide additional protection against shorting between wire 56 and central tube 50.

Referring to FIG. 4H, atraumatic coil tip 30' can comprise a tip coil 608 having a rounded distal end or solder ball 610 and a core wire 604 extending through the tip coil and attached or extending from rounded distal end 610. Tube 602 secures tip coil 608 to central tube or twist mandrel 50. Tube 602 includes a slot 603 that opens at the proximal end of the tube to provide a passage for wire 56 so that the wire can pass through tube 602 after exiting tube 50 and then extend proximally where it passes between tube 500 and sleeve 84 and then between tube 502 and sleeve or cover 504. Wire 56 is secured to sleeve 84 and tube 500 by applying and curing epoxy therein. The distal end of wire 56 is secured to twist mandrel 50 as well as to insulative tube 600 and slot 603 in tube 602 by applying and curing epoxy. Tube 602 is bonded (e.g., with solder and epoxy) to central tube or twist mandrel 50 and soldered to tip coil core wire 604. Tip coil 608 is soldered to tip coil wire 604 and to the distal end of tube 602. An insulative tube or sleeve 600 is then positioned over tube 602 and a distal portion of distal latch wire 56 to surround tube 602 and wire 56. The sleeve 600 is secured to tube 602 and wire 56 with, for example, epoxy. In one embodiment, tip coil 608 is platinum, core wire 604 is stainless steel, insulative tube 600 is polyimide tubing, and distal latch wire 56 is polyimide coated stainless steel wire.

Referring to FIG. 4I, a variation of tube 602 is shown and designated with reference number 602'. Tube 602' includes a slot 603' that extends its entire length providing more access to tip coil wire 604 so that tip coil wire 604 can be welded to tube 602' instead of soldering.

Figure 5:
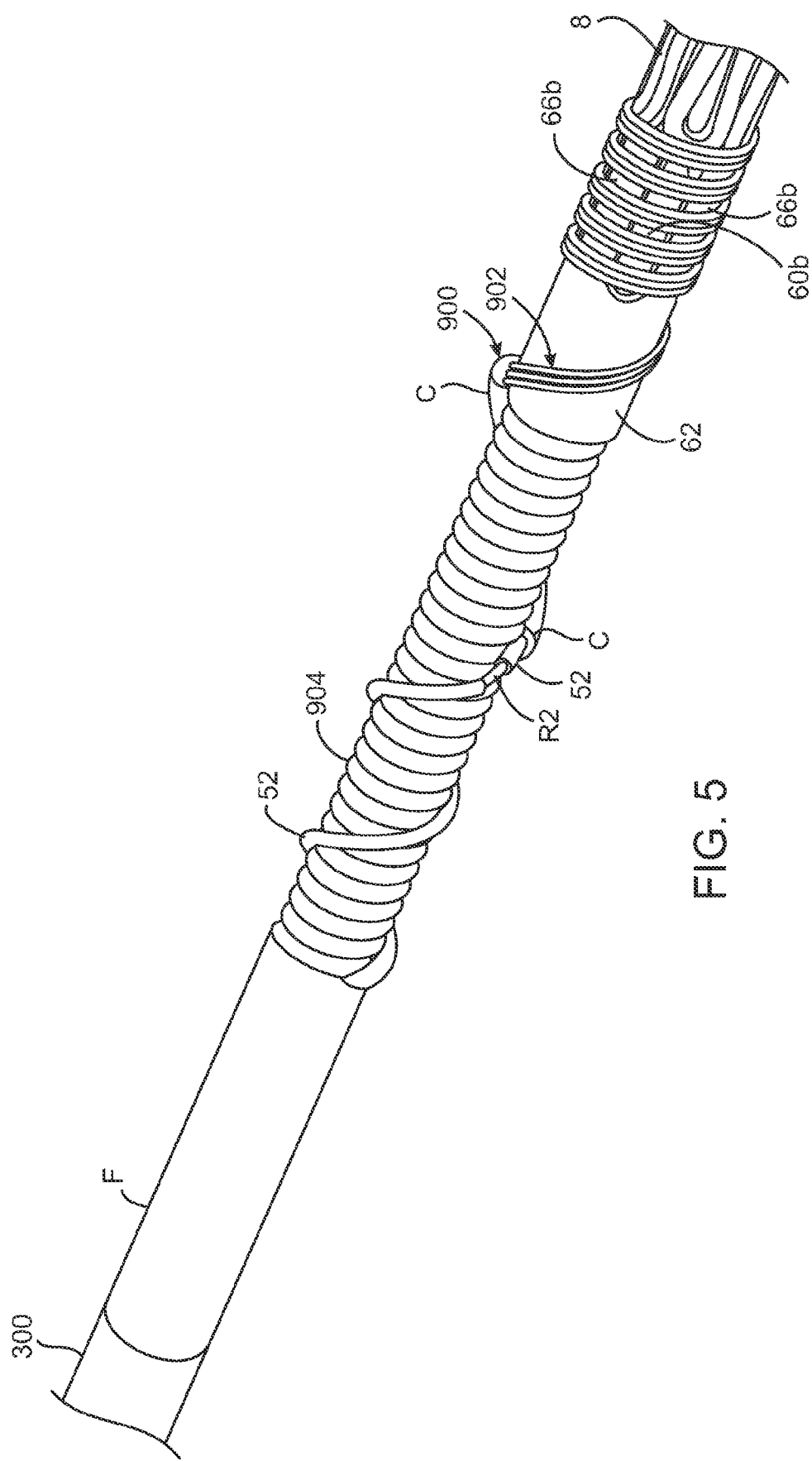
FIG. 5 is perspective view of a portion proximal to FIG. 4A showing a releasable proximal stent restraint mechanism according to one embodiment of the invention.

Referring to FIGS. 5 and 5A, a proximal releasable stent restraint mechanism according to one embodiment of the invention is shown and generally designated with reference numeral 900. Proximal releasable stent restraint mechanism 900 includes connector "C," restraint 902, which is a exemplary embodiment of restraint 55 shown in FIG. 2, and at least a portion of lead 52 that includes electrolytically erodible section "R2" and extends from connector "C." In this embodiment, restraint 902 comprises a plurality of elongated members, filaments, or strands 902a,b,c. Although three elongated members, filaments, or strands 902a,b,c are shown, more can be used to increase the strength of the restraint 902. For example, six or eight filaments or strands can be used to form restraint 902. However, fewer filaments or strands than two can be used depending on the strength requirements and strength of the filaments. In one embodiment, lead 52 is polyimide coated stainless steel wire having the polyimide insulation sleeve stripped at section "R2" to expose the wire.

It should be understood, however, that other materials can be used to make lead 52 as would be apparent to one skilled in the art. Filaments or strands 902a,b,c can be electrically nonconductive members such as polyester sutures. Alternatively, the restraint can be one or more strand of other nonconductive materials such as plastic, silk, or polyester strands. Thus, lead 52 and filaments or strands 902a,b,c can be made from different material. Lead 52 can be an insulated conductor such as an insulated stainless steel wire (the stainless steel wire being conductive material), and filaments or strands 902a,b,c can made from nonconductive material. In a further alternative, the restraint can be a conductor since it is electrically disconnected or isolated from erodible section "R2" as will be described in more detail below. Further, since the connector connects restraint 902 and erodible section "R2" without electrically connecting restraint 902 and erodible section "R2," insulation for the restraint is not required, which advantageously reduces delivery profile. The restraint can also extend over a portion of the stent crown with this construction which does not use insulated wire as a restraint. This can advantageously reduce the profile of this region. On the other hand, if one were to use, for example, insulated stainless steel wire as the restraint, the stent struts could damage the insulation, which could result in undesirable electrical shorting.

Restraint 902 extends distally from connector "C" and is wrapped around proximal stent tabs or projections 60b, which are seated in proximal seat 62 between proximal fingers 66b. Stent 8 is in its radially compressed and twisted configuration. Lead 52 extends proximally from connector "C" and wraps around radiopaque marker 904, and then around central tube or mandrel 50 to transition tube 300 from which it extends for coupling to the power supply (see FIG. 5A). Radiopaque marker 904 comprises a wire or ribbon wrapped around central tube or mandrel 50. Coil marker 904 can be formed from platinum-iridium wire or ribbon, or any suitable material. It also should be understood that other radiopaque marker constructions can be used. Epoxy "F" is applied around lead 52 and central tube or mandrel 50 as shown to fixedly secure wire 52 to central tube or mandrel 50. As shown in FIG. 5A, transition tube 300 is chamfered to provide access therein for lead 52 and epoxy F extends over a distal portion of transition tube 300. A polymeric tube is shrink wrapped around 52 in the region indicated with reference character "SW." Epoxy can be applied at the proximal end of radiopaque marker 904 and proximal end of the shrink wrap to provide a smooth transition to the epoxy indicated with reference character "F."

Figure 6A:
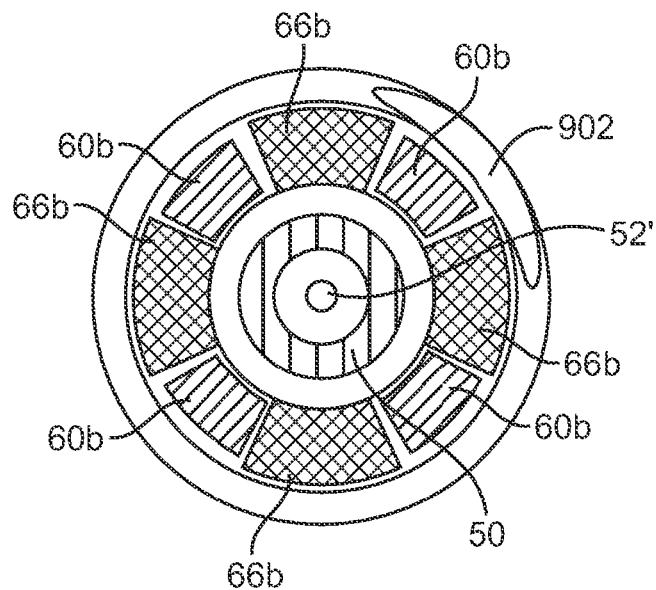
FIG. 6A is a sectional view taken along line 6A-6A in FIG. 5A.
Figure 6B:
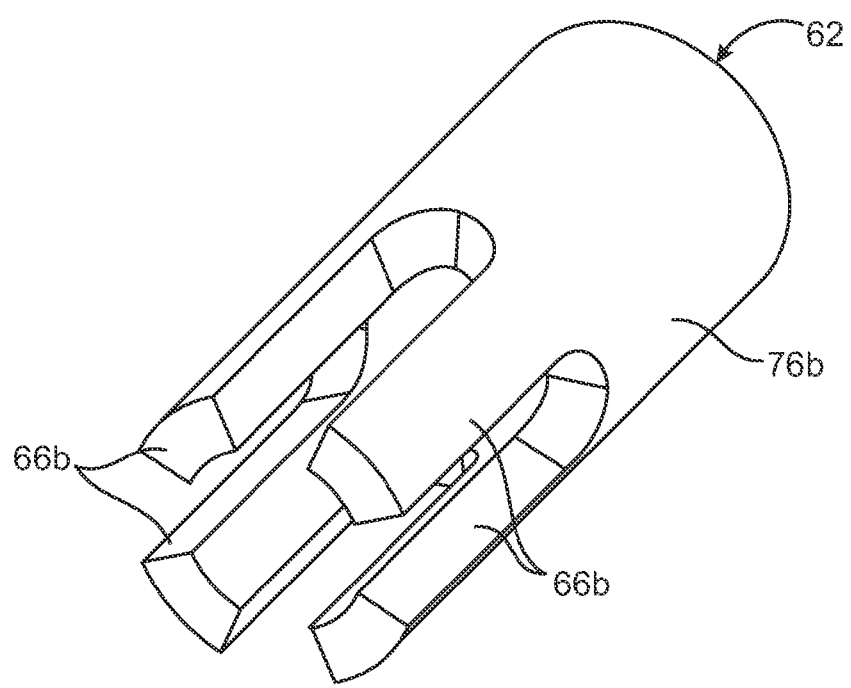
FIG. 6B is a perspective view of the stent tab seat of FIG. 6A.

Referring to FIG. 6A, which is a sectional view taken along line 6A-6A in FIG. 5A, a portion of restraint 902 is shown wrapped around proximal seat projections or tabs 60b and proximal seat fingers 66b. Distal lead 52' also is shown passing through the lumen of central tube or mandrel 50. FIG. 6B shows proximal seat 62, which includes seat body 76b and fingers 66b extending therefrom.

Figure 7:
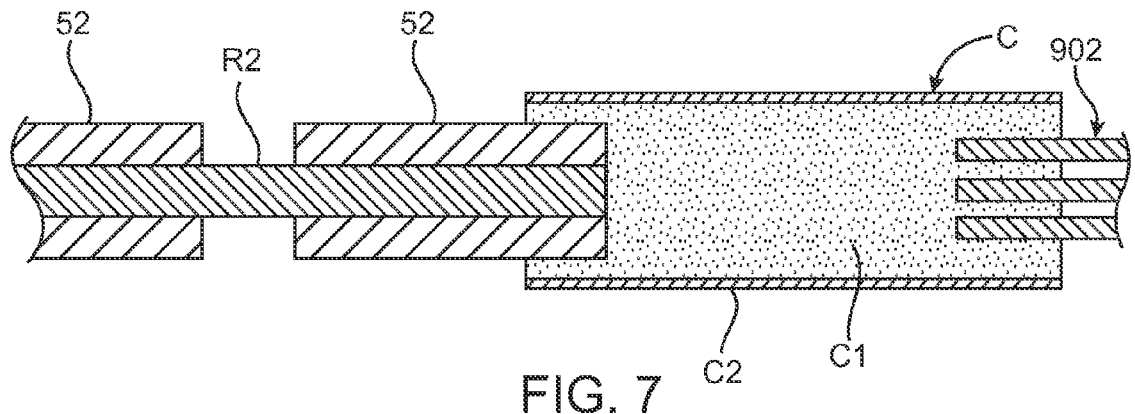
FIG. 7 is a longitudinal sectional view of a portion of the proximal releasable stent restraint mechanism of FIG. 5.

Referring to FIG. 7, a longitudinal section view of a portion of the proximal releasable stent restraint mechanism embodiment illustrated in FIG. 5 is shown. In this embodiment, connector "C" comprises an electrically nonconductive member C1 having a proximal end and a distal end. The distal end of lead 52 is connected to or embedded in nonconductive member C1 and the proximal end of restraint 55a is connected to or embedded in the distal end of nonconductive member C1. The proximal end of the restraint and the distal end of lead 52 are spaced from one another so that they are electrically isolated from one another through nonconductive member C1. Nonconductive member C1 electrically disconnects restraint 902 from erodible section "R2" and can comprise any suitable material such as epoxy and can be encased in tubing "C2," which can be polyimide tubing. However, when the restraint is an electrically nonconductive material as described above, connector "C" need not include a nonconductive member. Connector "C" can be a metal tube that is positioned around the ends of lead 52 and the restraint and crimped to secured the ends together.

Figure 8:
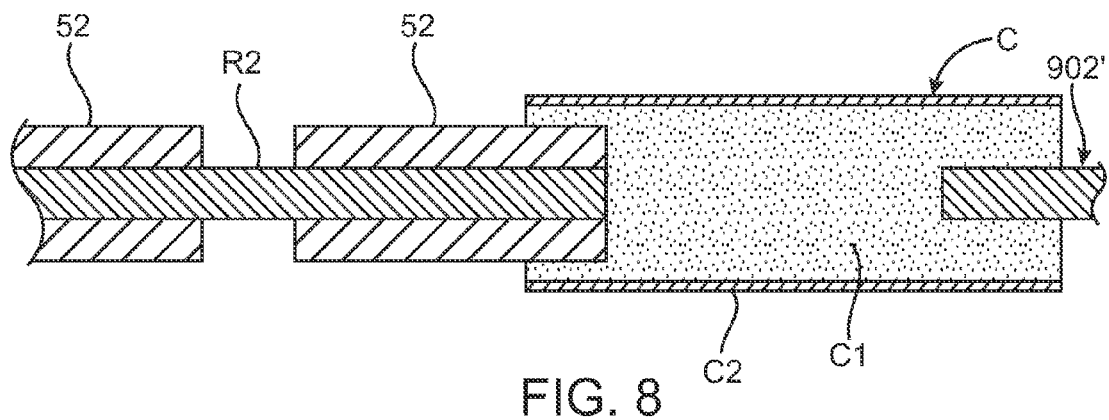
FIG. 8 is variation of the mechanism shown in FIG. 7.
Figure 9:
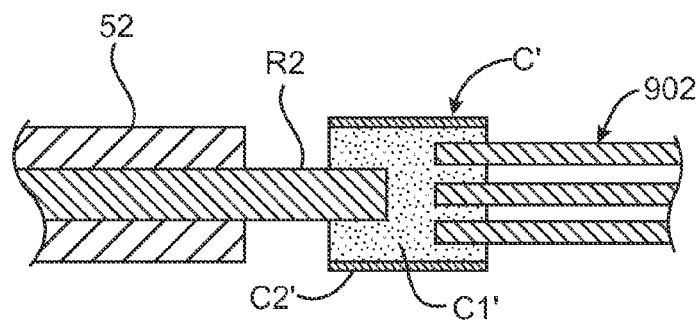
FIG. 9 is a longitudinal sectional view of another proximal releasable stent restraint mechanism embodiment.
Figure 10:
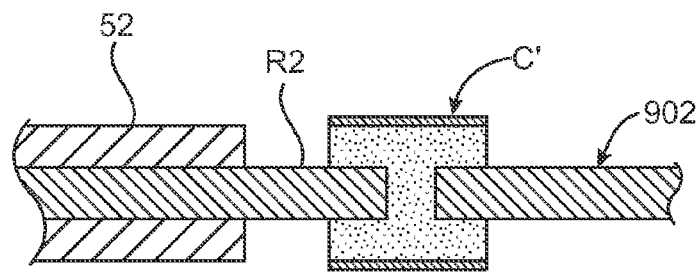
FIG. 10 is a variation of the embodiment of FIG. 9.

The embodiment shown in FIG. 8 is the same as that shown in FIG. 7 except that restraint 902' is formed by a single elongated member, filament, or strand as compared to restraint 902, which has a multi-elongated member, filament, or strand construction. The embodiment shown in FIG. 9 is the same as that shown in FIG. 7, except that the connector C' is shorter and the distal end of insulated lead 52 has been completely stripped of insulation and the bare wire embedded in nonconductive member C1'. The embodiment of FIG. 10 is the same as that shown in FIG. 9 except that the restraint 902' is formed by a single elongated member, filament, or strand.

Figure 11A:
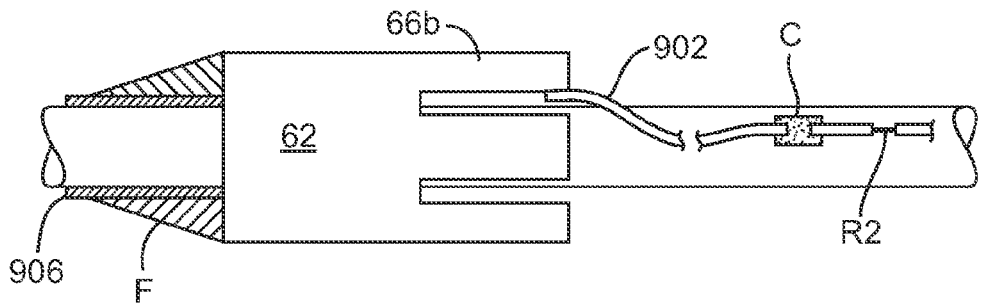
FIGS. 11A and 11B diagrammatically illustrate mounting a releasable stent restraint mechanism to the proximal stent seat according to the invention where the stent is not shown for purposes of simplification.
Figure 11B:
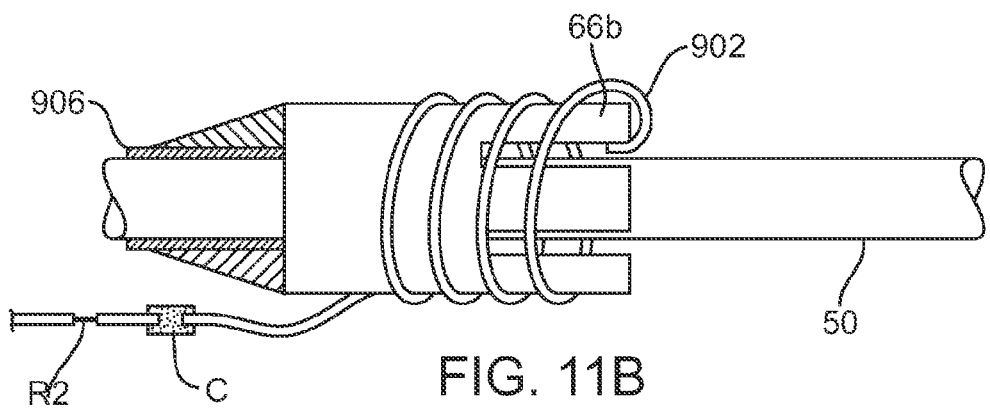

Referring to FIGS. 11A and 11B where the stent is not shown for purposes of simplification, mounting proximal releasable stent restraint mechanism 900 to the proximal stent seat will be described. The distal end of restraint 902 is secured under one of fingers 66b using for example, epoxy. Restraint 902 is then wrapped around fingers 66B and seat 62 and is connected to lead 52 through connector "C" and lead 52 is wrapped around marker 904 and a portion of central tube or mandrel 50 where is secured to central tube or mandrel 50 as shown in FIG. 5A. Seat 62 is secured to tube 50 with any suitable means such as solder. Insulation tube 906, which can be polyimide tubing, can secured to central tube or mandrel 50 (with any suitable material such as epoxy) proximal to seat 62. However, this tube is optional.

Figure 12:
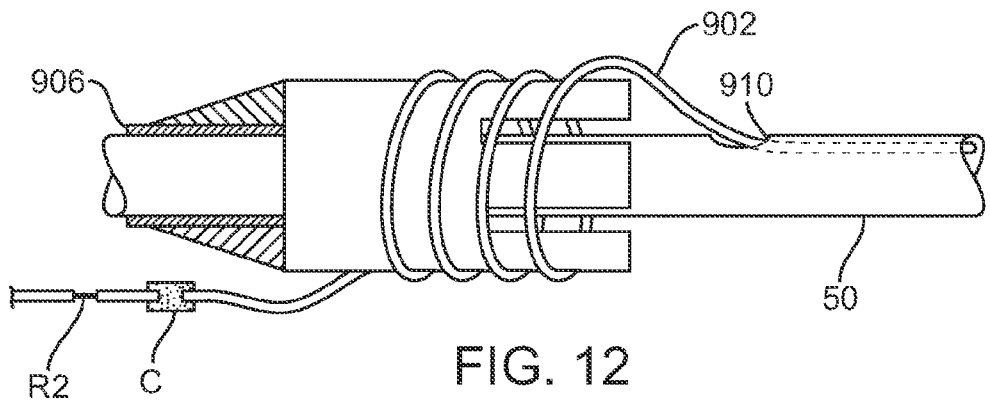
FIG. 12 illustrates a variation in the mount illustrated in FIGS. 11A and 11B.

Referring to FIG. 12, a variation of the mounting arrangement shown in FIGS. 11A and 11B is shown where the distal end of restraint 902 is passed through opening 910 formed in central tube or mandrel 50 and epoxy inserted in the opening to secure the distal end of restraint 902 to central tube or mandrel 50.

Figure 13:
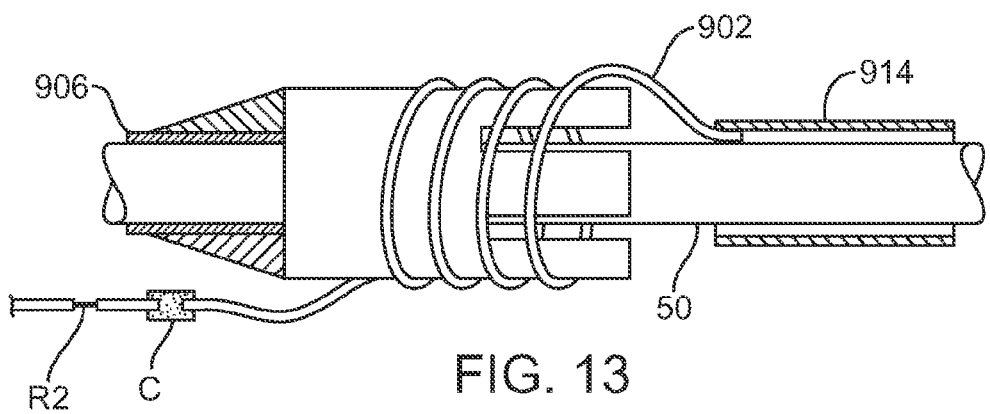
FIG. 13 is a further variation of the mount illustrated in FIGS. 11A and 11B.

Referring to FIG. 13, a further variation of the mounting arrangement shown in FIGS. 11A and 11B is shown where anchor tube 914, which can be made from polyimide tube, is positioned over central tube or mandrel 50, the distal end of restraint 902 positioned between anchor tube 914 and central tube or mandrel 50, and epoxy placed inside anchor tube 914 to secure the distal end of restraint 902 to anchor tube 914 and central tube or mandrel 50. As apparent from the foregoing, the epoxy also secures the anchor tube to central tube or mandrel 50.

Figure 14A:
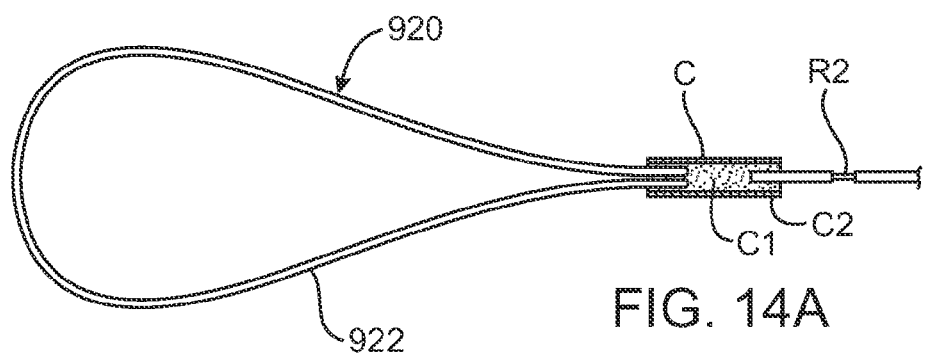
FIG. 14A is a partial sectional view of another proximal releasable stent restraint mechanism according to the invention.
Figure 14B:
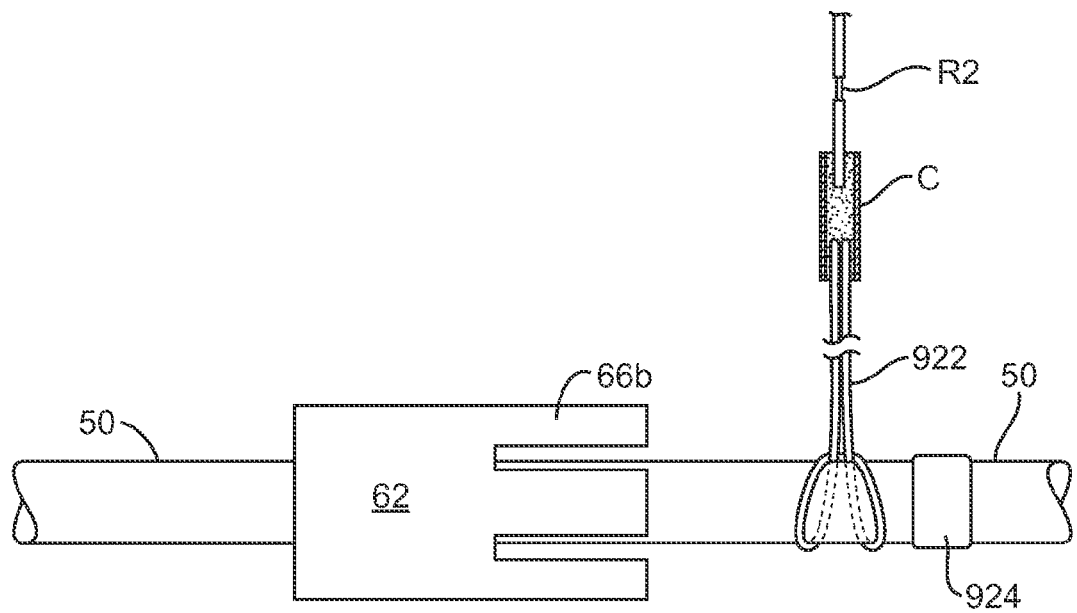
FIGS. 14B-14C illustrate mounting the mechanism of FIG. 14A (the stent not being shown for simplification), where
Figure 14C:
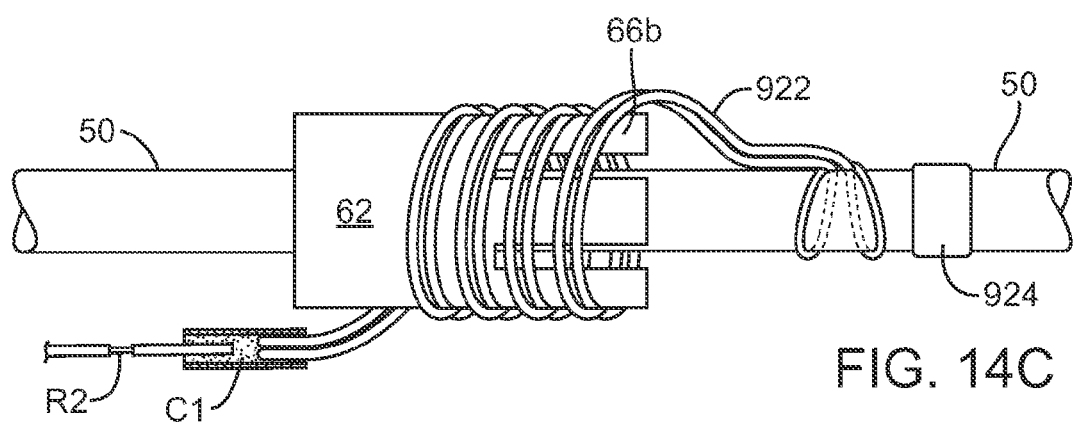

Referring to FIGS. 14A-C, another proximal releasable stent restraint mechanism according to the invention is shown in partial cross-section and generally designated with reference numeral 920. Proximal releasable stent restraint mechanism 920 is the same as mechanism 900 except the restraint 902 is replaced with loop shaped restraint 922. Loop shaped restraint 922 can be formed by taking a single elongated member, filament, or strand having first and second ends and then securing those ends to nonconductive member C1 as described above (e.g., the single strand ends can be embedded in epoxy filled tube C2). Loop shaped restraint 922 can be formed from the same materials as restraint 902.

Figure 15B:
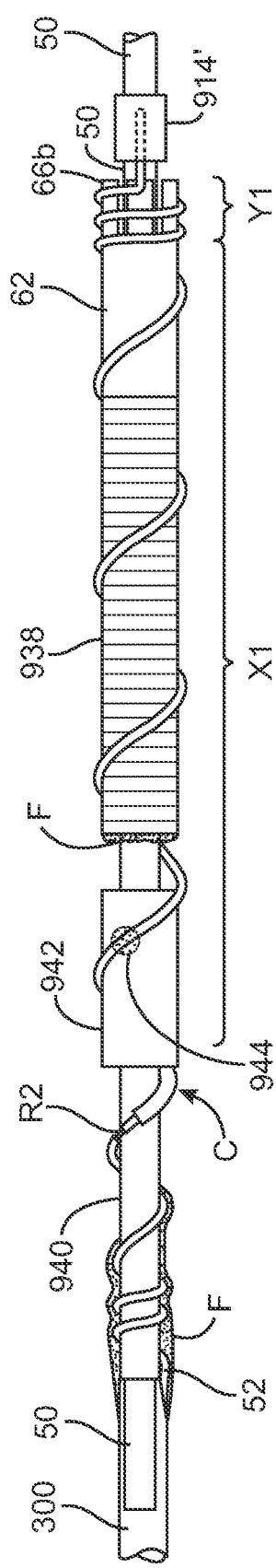
FIG. 15B illustrates the mechanism of FIG. 15A mounted on a delivery guide (the stent not being shown for simplification) prior to release.

Referring to FIGS. 14B-14C where the stent is not shown for simplification, mounting of proximal releasable stent restraint mechanism 920 will be described. FIG. 14B shows the free end of loop shaped restraint 922 looped around central tube or mandrel 50 and through itself to form a knot that secures releasable stent restraint mechanism 920 to the central tube or mandrel 50. A stopper or blocker 924 is fixed to central tube or mandrel 50 to prevent restraint 922 moving distally beyond the stopper or blocker. Stopper or blocker 924 can be in the form of a tube and made from any suitable material such as polyimide. FIG. 14C shows the restraint 922 further wrapped around fingers 66b and seat 62 and is connected to lead 52 through connector "C" and lead 52 is wrapped around marker 904 and a portion of central tube or mandrel 50 where is secured to central tube or mandrel 50 as shown in FIG. 5A Referring to FIGS. 15A-C, another proximal releasable stent restraint mechanism embodiment is shown and generally designated with reference numeral 930. Proximal releasable stent restraint mechanism 930 includes connector "C," which is the same as that described above, restraint 932, which extends from connector "C," and at least a portion of lead 52, which includes electrolytically erodible section "R1" and extends from connector "C." Restraint 932 includes an attachment portion 934 and a coil portion 936, which has an end that is secured to connector "C" or is embedded in connector "C" in the same manner as the other restraints described above. In the illustrative embodiment, attachment portion 934 is an elongated straight member or portion. Attachment portion 934 is wrapped around the proximal seat 62 and its seat fingers 66b as will be described below and therefore can be referred to as a wrap portion. It should be understood that although attachment portion is shown with a straight configuration or shape, it can have other configurations or shapes as would be apparent to those of ordinary skill in the art. Restraint 932 can be made from any suitable material. It can be made from wire made from shape memory alloy or elastic material or wire so that it tends to return to its memory shape (FIG. 15A) after being released from a deformed shape (e.g., that shown in FIG. 15B). As is well known in the art, shape memory material has thermal or stress relieved properties that enable it to return to a memory shape. Further, restraint 932 can be made from shape memory alloy material such nitinol wire and provided with a memory set shape configuration as shown in FIG. 15A. In this case, restraint 932 can be made by wrapping a nitinol wire having a diameter in the range of about 0.001 to 0.002 inch, and preferably 0.015 inch, and wrapping it around a mandrel having a diameter in the range of about 0.011 to 0.012 inch, and preferably 0.0115 inch to form coil 936. Restraint 932 (including straight leg 934 and coil 936) can then heat treated to permanently set its shape as shown in FIG. 15A. More specifically, the coil and mandrel can be heat-treated in either a convection oven or bath at a temperature range of 500 to 550° C., preferably 525° C., for a duration of about 10 to 15 minutes, and preferably 12 minutes. The restraint is then quenched in a water bath, which is at room temperature. The restraint with its memory set shape as shown in FIG. 15A can then be pickled to remove oxides as is known in the art.

Referring to FIG. 15B, proximal releasable stent restraint mechanism 930 is shown mounted on the delivery guide and loaded for release. In assembly, anchor tube 914', which has the same construction as tube 914 and can be made from polyimide tubing is positioned over central tube or mandrel 50, the distal end of attachment portion 934 is positioned between anchor tube 914' and central tube or mandrel 50, and epoxy placed inside anchor tube 914' to secure the distal end of attachment portion 934 to anchor tube 914' and central tube or mandrel 50. As apparent from the foregoing, the epoxy also secures the anchor tube to central tube or mandrel 50.

Seat 62 and proximal releasable stent restraint mechanism 930 are then positioned over central tube or mandrel 50 and the seat secured to central tube or mandrel with, for example, solder. Radiopaque marker coil 938, which has the same construction as marker coil 904, is placed over central tube or mandrel 50 and soldered to seat 62 and mandrel 50. That is coil 938 can be made from platinum iridium wire or ribbon and coiled into the cylindrical configuration shown to form a marker. Coil 938 can be made from wire having a thickness of 0.002 inch and wound to form a cylinder with an outer diameter of 0.009 inch and a length of 0.060 inch. Spin tube 942 is positioned next to marker 938 so that it is free to rotate and move axially along mandrel 50. Spin tube 942 can be a stainless steel tube with an inner diameter of 0.0055 inch, outer diameter of 0.009 inch, and a length of 0.030 inch. An insulation tube 940, which can be polyimide tubing, is then positioned over central tube or mandrel 50 and bonded to mandrel 50 with epoxy F. Insulation tube 940 can have an inner diameter of 0.0061 inch, an outer diameter of 0.0094 inch and a length of 0.080 inch. Attachment portion 934 is wrapped around the seat fingers 66b and stent projections or tabs (not shown) and seat 62. The coil is then wrapped (wound) around any remaining portion of seat 62 and then around radiopaque marker 938 and spin tube 942. A portion of wire 52, which extends from connector "C" is then epoxied to insulation tube 940 as shown with reference character "F." Epoxy also is applied to where insulation tube 940 abuts transition tube 300, which is chamfered to receive wire 52. Coil 936 is then secured to spin tube 942 with epoxy or solder at 944.

Figure 15C:
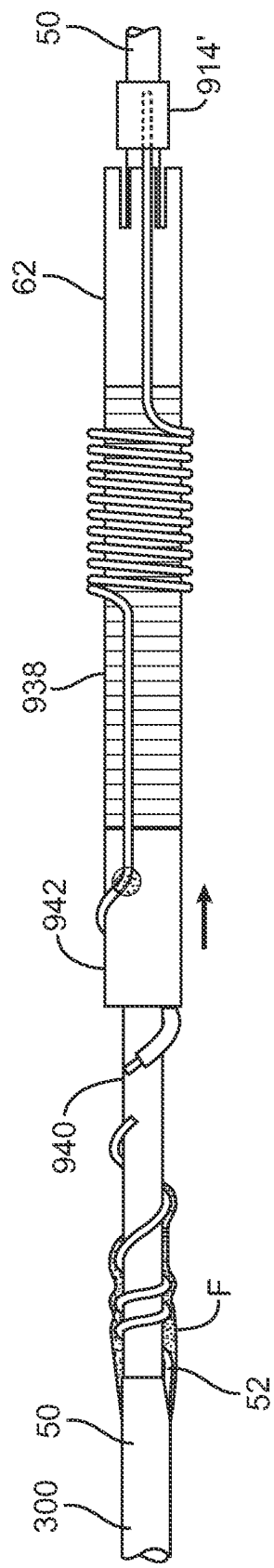
FIG. 15C shows the mechanism of FIG. 15B after release.

Referring to FIG. 15C, proximal releasable stent restraint mechanism 930 is shown in a released state after erodible section "R2" has been fully eroded. Upon erosion of erodible section "R2," spin tube 942 is free to rotate and move distally as shown. This allows coil portion 936 to move toward its memory set configuration. As coil portion 936 moves toward its memory set configuration shown in FIG. 15A, its spring force aids in pulling attachment portion 934 back toward its pre-wrapped or original configuration, which in the illustrative embodiment of FIG. 15A is straight, thereby allowing the stent end projections or tabs to radially expand out from seat 62. In other words, when erodible section "R" is eroded coil or coil portion 936 moves toward its unexpanded relaxed configuration and pulls the wrapped attachment portion to an unwrapped configuration.

Referring to FIGS. 16A-G, a method of stent loading a stent onto delivery guide 22 or assembling the delivery guide will be described. In this method, the stent is compressed by hand, with an automated "crimper" such as produced by Machine Solutions, Inc., or otherwise, without a substantial twist imparted thereto. The stent can be compressed by virtue of the act of loading it into a tube, or loaded into a tube after being compressed by a machine. In any case, the tube or sleeve that it is loaded into will generally be close in diameter to its final size when secured upon or the delivery guide. By "close" in diameter, what is meant is that it is within at least about 33%, or more preferably within about 25% to about 10%, or even within about 5% or substantially at its final diameter. Then, with the stent so constrained, it is twisted from either one or both ends before or after partial or full attachment to the delivery guide.

The sleeve can comprise a plurality of separate pieces or segments (most conveniently two or three). As such, the individual segments can be rotated relative to one another to assist in twisting the stent. In addition, axial manipulation of the relation of thin individual segments can be employed to allow the implant to bulge outwardly over one section. The foreshortening caused by this action can then allow positioning and then axially loading end interface members by manipulating the segments to collapse the bulging.

The figures illustrate a process of loading a delivery guide using only a single restraint sleeve 700. To carry out the additional acts above, or to reduce the degree to which the stent must twist inside a single sleeve, sleeve 700 can be broken into a number of segments (before or after loading a compressed stent therein).

Figure 16A:
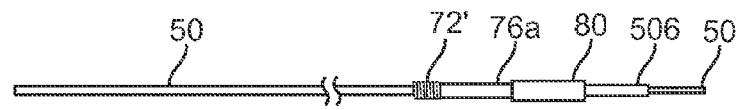

Referring to FIG. 16A, central tube 50 is provided with distal seat body 76*a* from which fingers 66*a* extend and to which connector tube 80 is fixedly secured. Connector tube 80 is fixedly secured to tubular latch mount 506.

Figure 16B:
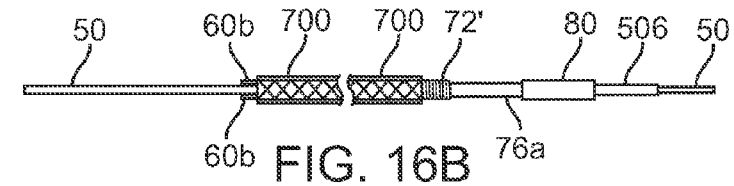

Referring to FIG. 16B, stent 8 is then radially compressed and introduced into one or more sleeve(s) 700 depending on the length of the stent and considerations described above. Distal tabs 60*a* are seated between fingers 66*a* and under coil 72' slid over the tabs to prevent them from radially expanding.

Figure 16C:
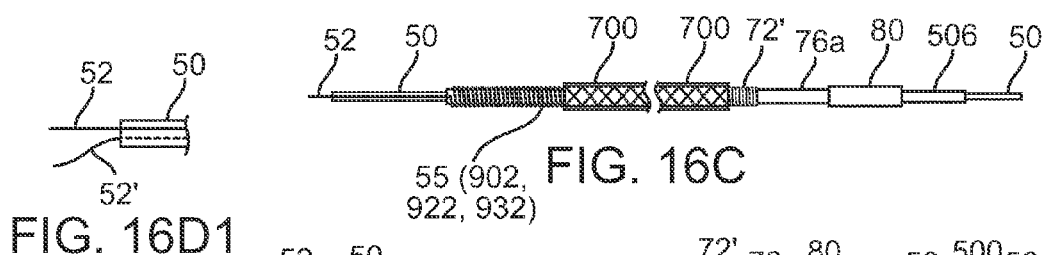

Referring to FIG. 16C (and FIGS. 6A and 6B), proximal seat 62, which comprises proximal seat body 76*b* and fingers 66*b*, which extend from proximal seat body 76*b*, is slid over central tube 50. Seat 62 is slid on central tube or mandrel 50 from the proximal end of central tube or mandrel 50 and secured thereto with for example solder. Restraint 55, which can correspond to restraint 902, 922, or 932, is wrapped around seat 62 and the distal end of restraint 55 secured to seat 62 or central tube 50 as described above to restrain tabs 60*b* and prevent them from expanding radially outward.

Figure 16D:
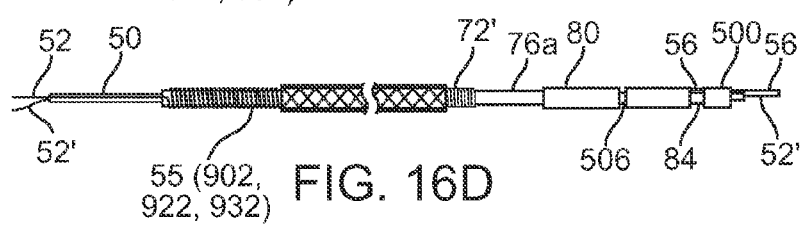

Referring to FIG. 16D, the tubes of latch assembly 71 (tubes 500, 502, 504, and 84) are added and wire 56, which has been secured to tubes 502 and 504 as described above, is extended proximally through tube 50 where it is referred to as lead 52'. FIG. 16D1 is an enlarged view of the proximal end portion of the apparatus shown in FIG. 16D.

Figure 16E:
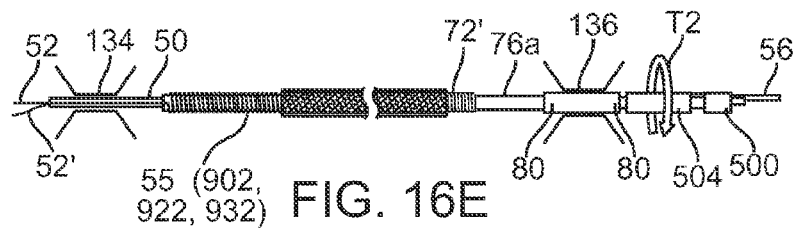

Referring to FIG. 16E, proximal clamp 134 is used to clamp a portion of the delivery guide proximal to proximal seat 62 in a fixed position. Distal clamp 136 is used to clamp tube 80 in a fixed position. Tube 80 is twisted by twisting or rotating clamp 136 as shown with arrow T2 to twist stent 8 and further reduce the transverse profile of stent 8. Prior to twisting, wire 56 was secured to and between tubes 502 and 504 and between tubes 84 and 500 as described above. Tube 84 is secured to central tube 50 after twisting to fix the distal end of latch assembly 71 to central tube 50 and prevent rotation of seat 64 and untwisting of the stent.

Figure 16F:
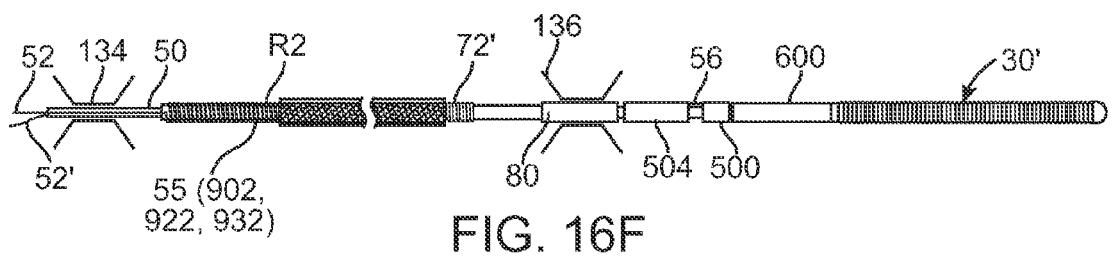

Referring to FIG. 16F, wire 56 is secured to central tube or mandrel 50 with epoxy and distal tip 30' is mounted to central tube 50 as described above.

Figure 16G:
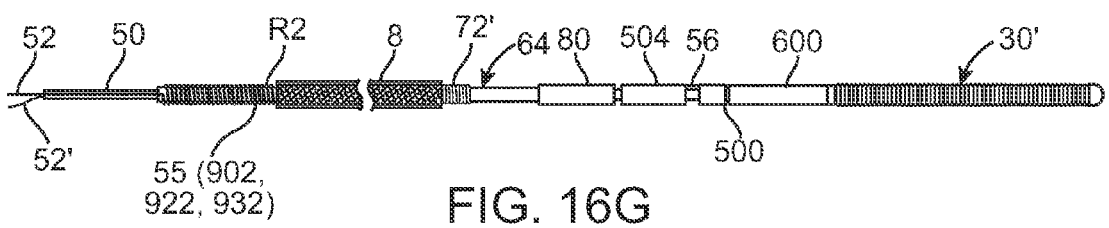

Referring to FIG. 16G, the clamps are released and stent 8 places the portion of distal latch wire 56 where electrolytic sacrificial link R1 is situated in torsion. In other words, distal latch wire 56 prevents stent 8 from untwisting.

For stent deployment, power first is provided to sacrificial link "R1." When sacrificial link R1 breaks, members 72', 64, 80, 502, 504 and 506 rotate together about central tube 50 because they are interconnected (also see FIGS. 4E and 4F). However, tubes 500 and 84 do not rotate. As a result, stent 8, which is mounted in seat body 64, untwists and shortens. As stent 8 shortens, tabs 60*a* are withdrawn from seat 64 and the distal end of the stent radially expands. Power is then provided to sacrificial link "R2." When sacrificial link "R2" erodes or breaks, restraint wrap 55 loosens and proximal tabs 60*b* of stent 8 radially expand and become released from delivery guide 22 allowing the proximal end to radially expand.

Referring to FIG. 17, a delivery guide embodiment without the stent and distal coil tip secured thereto is diagrammatically shown to illustrate the transition from any one of the foregoing proximal stent restraints to body tube 162, which is electrically coupled to the power supply. For purposes of example, restraint 902 is shown. In sum, transition tube provides a transition for the delivery guide from the proximal end of central tube 50 to body tube 162 and core wire 164 as will be described in more detail with reference to FIGS. 17A-D.

FIGS. 17 and 17A-D illustrate features of the delivery guide directed to allowing the delivery guide to perform as a standard high-performance guidewire despite the increased system complexity. Referring to FIG. 17, the components selected capable of such use. The delivery guide includes a superelastic NiTi hypotube 162 (roughly 165 cm) over a taper-ground stainless steel core wire 164. Power leads 52 and 52' run through the hypotube and along core wire 164. The core wire is affixed (e.g., by soldering) to a distal superelastic NiTi "transition tube" 300 and through which leads 52 and 52' extend. Hypotube 162 can also be connected (e.g., soldered) to core wire 164. The stent and a far-distal atraumatic tip (not shown) are connected to center tube or mandrel 50, which can be a hypotube. Center tube 50 receives lead 52' within its lumen. Alternatively, element mandrel 50 can be formed as a solid mandrel and leads 52 and 52' run along its body (possibly protected by a polymeric sleeve).

Referring to FIGS. 17A-D further details are shown. Referring to FIG. 17A, epoxy "F" provides a transition between the transition tube 300 (FIG. 17B) and the radiopaque marker (e.g., marker 904). Referring FIG. 17B, the distal portion of transition tube 300 merges into the proximal portion of central tube or mandrel 50. Filler "F," which, for example, can be adhesive (e.g., epoxy) or solder, and is formed into a generally cylindrical shape and encapsulates wire 52, terminates along transition tube 300 as shown in FIG. 17B.

Transition tube 300 provides kink resistance and the desired torque transmission and in the illustrative embodiment, is in the form of superelastic material such as nitinol tubing. However, it can be made in other forms than that shown and can be made from superelastic materials other than nitinol. Typically, central tube or mandrel 50 extends into transition tube a distance of about 10-20 mm and transition tube 300 can be provided with a hydrophilic coating. This transition zone where central tube or mandrel 50 overlaps superelastic transition tube 300 provides a transition between a relatively stiff region distal thereto and a relatively flexible region proximal thereto (more flexible than the relatively stiff region proximal to the transition) and provides for desirable torque transmission and pushability.

Referring to FIG. 17C, tube 300 extends proximally and has a chamfered proximal end where the tapered portion of corewire 164 is positioned and secured to transition tube 300 with solder and epoxy and a chamfered distal end (FIG. 17B). Leads 52 and 52' and corewire 164 extend proximally to the power connection as will be described in more detail below. Corewire 164 provides a path for ground and in one embodiment is high strength stainless steel (e.g., 304 or MP35). A protective sleeve (not shown) can be provided to enclose leads or wires 52 and 52' and the tapered portion of corewire 164 to protect the leads or wires from the edge of the chamfered portions of tube 300. Wire 52 can be arranged to extend out from the region between tube 50 and chamfer at the distal end of tube 300. That region can be filled with filler F as shown in FIG. 17A and this filler can be epoxy and/or solder. Tube 162 extends from the proximal end of superelastic tube 300 to the power connection as well. Tube 162 also is selected to provide flexibility and pushability and in one example is nitinol with a PTFE coating.

The illustrated construction in zone "C" which extends from the distal end of tube 162 to central tube or mandrel 50 provides a relatively flexible region in the delivery guide. Zone C has a length of 15-25 cm and more typically a length of 19-22 cm. Zone "B," which has a length of 10-20 mm and in one embodiment has a length of 10 mm and extends from the distal end of tube 162 in near the proximal end of tube 300 to the beginning of the taper of corewire 164 provides a transition to relatively stiff region zone "A," which with corewire 164 is stiffer than zone "C." Zone A, which extends about 145-175 cm and extends in one example 155 cm, is the stiffest section and provides excellent transmission of torque and pushability to the distal end of delivery guide 22 of delivery system 20. Zone A extends proximally and is coupled to the power supply.

FIG. 17D is a sectional view of zone A taken along line 17D-17D in FIG. 17C. Zone B is less stiff than zone A, but more stiff than zone C and zone D. Zone C also is more flexible or less stiff than zone D. Zone D extends from the proximal end of central tube 50 (FIG. 17B) distally to the proximal end of marker 904 (FIG. 17C). The region of delivery guide 22 containing the stent seats and stent release mechanisms are stiffer than the stent and the portion of coil tip 30' in zone E (FIG. 4F) is very flexible and radiopaque to provide an atraumatic lead structure for the stent and delivery guide 22. Zone E has a length of about 1 cm to about 4 cm, and more typically has a length of 2-3 cm.

A table illustrating stiffness parameters according to one embodiment of the inventions is provided below using a three point test. Generally speaking zone A, which typically has a length of about 145-165 cm is the stiffest region of delivery guide 22. Zone B is less stiff the Zone A and Zone C is more stiff than Zone E, the most floppy or flexible zone.

| REGION OF DELIVERY GUIDE 22 | BENDING STIFFNESS (lbf-in2) |
|---|---|
| Zone A Composite high strength stainless steel corewire 164, with superelastic tube 162; and leads 52, 52' | 0.0140-0.0220 |
| Zone B Composite tapered corewire 164 and superelastic tube 162 | 0.007-0.013 |
| Zone C Composite superelastic tube and leads 52, 52' | 0.005-0.007 |
| Zone D Composite superelastic tube 300 and stainless steel central tube 50 followed by stainless steel central tube 50 surrounded by lead wire 52 and housing lead 52' and housed in filler such as epoxy. | 0.003-0.005 |
| Proximal Stent Restraint (Cross section of FIG. 6A) | 0.0025-0.0028 |
| Stent | 0.0008-0.001 |
| Tube 600 (its entire length) composite tube 600, tube 602, tube 604 and wire 52') | 0.001-0.0015 |
| Zone E (From the distal end of 602 and 600 to the distal end of ball 610) | 0.0001-0.0005 |

Regarding the power connection to leads 52 and 52', Leads 52 and 52' can be connected to the power supply in any suitable manner. One example is described in detail in U.S. patent application Ser. No. 11/957,211, filed Dec. 14, 2007, entitled Stent Systems and published as U.S. Patent Application Publication No. 2008/0221666, the disclosure of each of these references is incorporated by reference herein in its entirety (See e.g., FIGS. 11A-D and the corresponding description therein).

Figure 18:
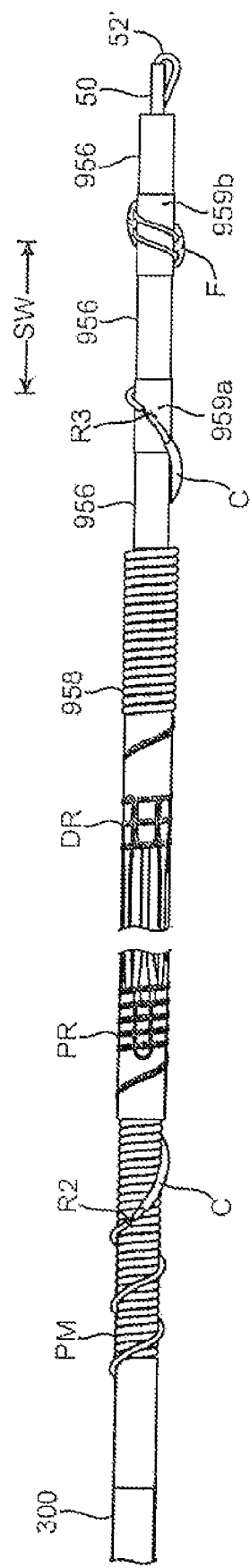
FIG. 18 illustrates another delivery guide embodiment according to the invention.

Referring to FIG. 18, another delivery guide embodiment is shown and corresponds to the delivery guide embodiment of FIG. 2 except that distal releasable stent restraint mechanism has a distal restraint "DR" in the form of a wrap or coil in any one of the embodiments described above in connection with FIGS. 5, 5A, 14A-C, and 15A-C. The proximal releasable stent restraint mechanism can correspond to any of the proximal releasable restraint mechanisms with proximal restraints described above with the proximal restraint designated as "PR." The proximal portion of the embodiment illustrated in FIG. 18 also has a proximal marker "PM," which can have the same construction as marker 904 of FIGS. 5 and 5A.

Referring to FIG. 18A, the distal releasable stent restraint mechanism shown in FIG. 18 will be described. Distal releasable stent mechanism 950 includes connector "C," which the same as connector "C" described above, restraint 952, which can be a single elongated member, filament, or strand or be formed of multiple elongated members, filaments, or strands (e.g., it can be three elongated members, filaments or strands as shown in FIG. 5 or it can be made for fewer or more elongated members, filaments, or strands as described above), and at least a portion of lead 52' that includes electrolytically erodible section "R3" and extends from connector "C" in the same manner that any of the proximal restraints described above extend from connector "C."

In assembly, distal seat 64 is mounted on central tube or mandrel 50 and an extension tube 956 secured to the distal end of distal seat 64 (e.g., by welding and gold solder). Radiopaque marker 958 is provided over the proximal portion of extension tube 956 and secured to distal seat 64 with solder or epoxy. Marker 958 also is soldered or epoxied to extension tube 956. Insulation tubes 959a and 959b, which can be formed from polyimide tubing, are provided over extension tube 956 as shown. A restraint holding member 953, which can be in the form of a tube assembly, holds the proximal end of the restraint. In the illustrative embodiment, restraint holding member 953 includes an outer tube 953a and an inner tube 953b both of which can be made from polyimide tubing. Restraint holding member 953 is mounted on central tube or mandrel 50 such that it is free to rotate and move axially along central tube or mandrel 50. A stopper or blocker 954, which can be in the form of a polyimide tube, is secured to central tube or mandrel 50 proximally of restraint holding member 953 to limit proximal translation of member 953. Stopper or blocker also can have the same construction as stopper or blocker 924. The proximal end of restraint 952 is secured between tubes 953a and 953b with epoxy or other suitable means. The restraint is wrapped around distal seat fingers 66a (between which the distal stent projections or tabs 60a would be placed) to secure the stent distal projections in the distal seat and restrain radial expansion of the distal end of the stent. Restraint 952 is further wrapped around marker 958 and extension tube 956. Connector "C" and "R3" are wrapped over insulation tube 959a and then lead 52' wraps over a portion of insulation tube 959b where it is epoxied to insulation tube 959b as shown with reference character "F."

Figure 18B:
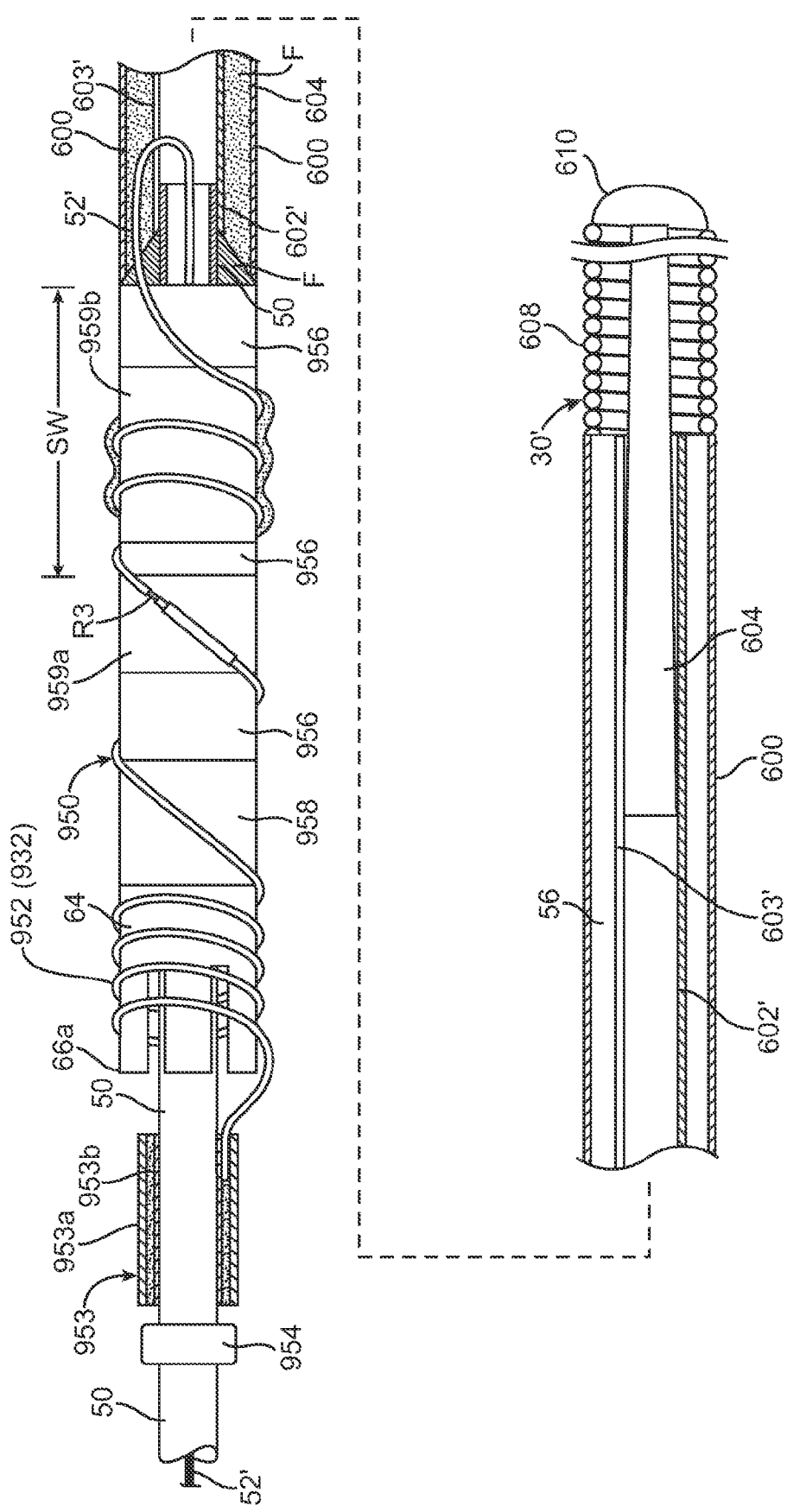
FIG. 18B is a partial sectional view of the distal releasable stent restraint mechanism of FIG. 18 with its distal end secured to the delivery guide.

Referring to FIG. 18B, lead 52' is passed through the distal end of center tube or mandrel 50 and fed proximally therethough for coupling with the power supply. Epoxy is used to secure lead 52' and the distal end of extension tube 956 to central tube or mandrel 50 after the stent is inserted in distal seat 64 and the distal seat rotated to twist the stent (the proximal seat having been fixed to central tube 50). A polymeric tube is shrink wrapped around 52' in the region indicated with reference character "SW." Sleeve 600 and distal tip 30' are secured to central tube or mandrel 50 as described above in connection with FIGS. 4F and 4I.

Proximal releasable restraint mechanism 930 also can be used as a distal releasable restraint mechanism. When restraint mechanism 930 is used as a distal releasable restraint mechanism it is mounted in the same manner as distal releasable restraint mechanism 950 is mounted as shown in FIGS.

18A and 18B where restraint 932 is shown in parentheses. Therefore, FIGS. 18A and 18B illustrate mounting restraint mechanism 930 as a distal releasable restraint mechanism. More specifically, attachment portion 934 of restraint 932 is secured in tube assembly 953 in the same manner as the proximal end of restraint 952. Attachment portion 934 forms about one wrap around fingers 66a. Then coil portion 936 is wrapped (wound) around the remaining portion of seat 64 (including fingers 66a), marker coil 958, and extension tube 956 in the same manner that restraint 952 is wrapped around those members. The connector "C" and lead 52' extending therefrom would be mounted in the same manner as shown in FIGS. 18A and 18B. Since the unwrapped coil portion 936 has a diameter larger than it has when it is wrap, it can expand when erodible section "R3" is eroded and broken. This allows the stent to be released and untwist and foreshorten. Stopper or blocker 954 can stop tube assembly 953 from moving proximally as attachment portion 934 straightens.

Figure 19A:
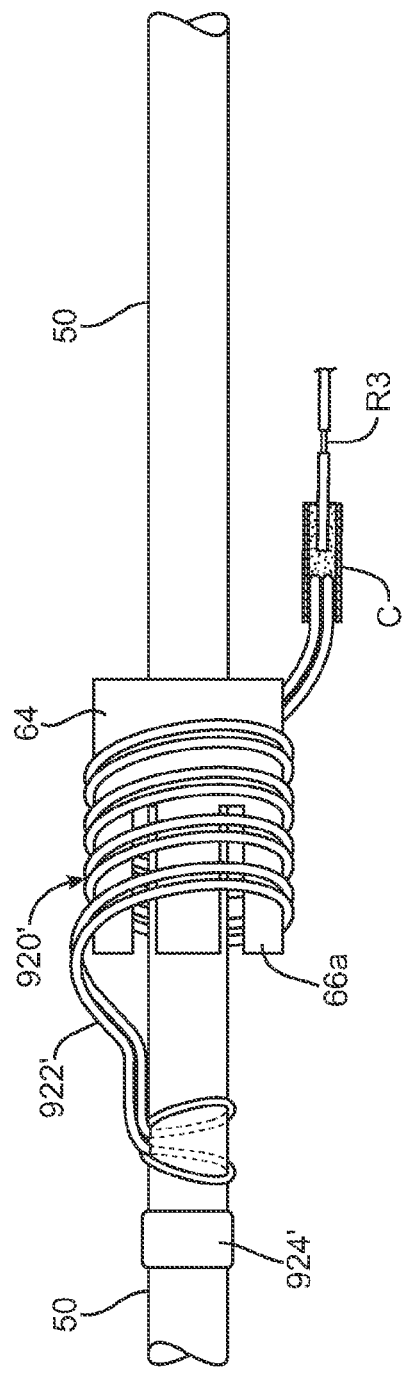
FIG. 19A is a partial sectional view of a variation of the distal releasable stent restraint mechanism of FIG. 18A.
Figure 19B:
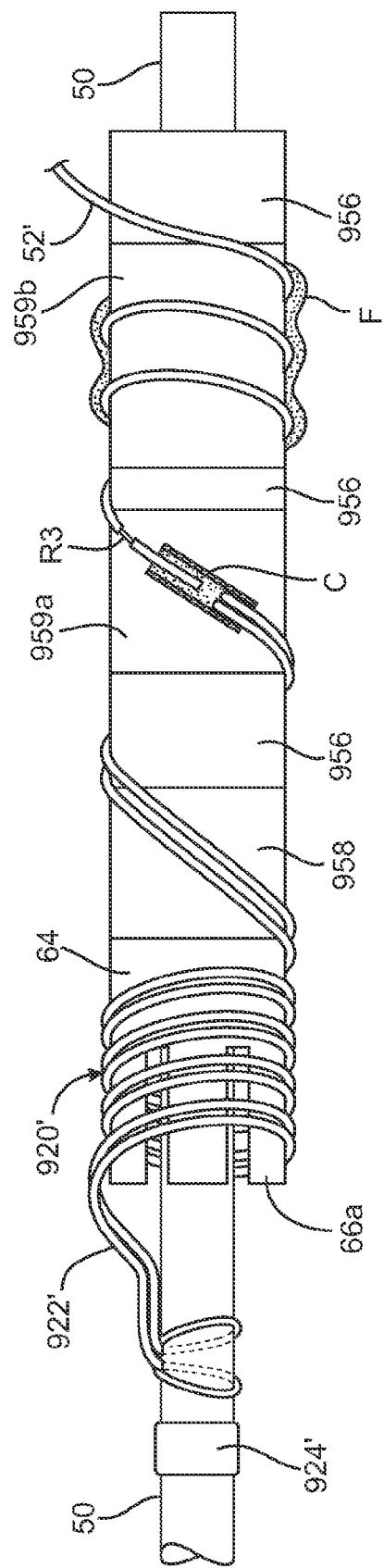
FIG. 19B is a partial sectional view of the distal releasable stent restraint mechanism of FIG. 19A with its distal end secured to the delivery guide.

Referring to FIGS. 19A and 19B, another distal releasable stent restraint mechanism that can be used instead of that shown in FIGS. 18A-C is shown and is designated with reference numeral 920'. Distal releasable stent restraint mechanism 920' is the same as mechanism 950 except the restraint 952 is replaced with loop shaped restraint 922' which is the same as loop shaped restraint 902 as shown in FIG. 14A. Distal releasable stent restraint mechanism 920' with loop shaped restraint 922' is mounted to central tube or mandrel 50 in the same manner as mechanism 950 except the proximal end of the loop shape restraint 922' is secured to central tube or mandrel 50 in the same manner as the distal end of proximal loop shaped restraint 922. A stopper or blocker 924', which can be polyimide tubing, is secured to central tube or mandrel 50 with epoxy or any suitable means to limit proximal movement of the portion of restraint 920' that is tied or knotted to central tube or mandrel 50.

Referring to FIGS. 20A-I, a method of loading the delivery guide of FIG. 18 will be described. For purposes of example, reference will be made to distal releasable stent restraint mechanism 950 illustrated in FIGS. 18A and 18B and proximal releasable stent restraint mechanism mounting arrangement shown in FIG. 13.

Figure 20A:
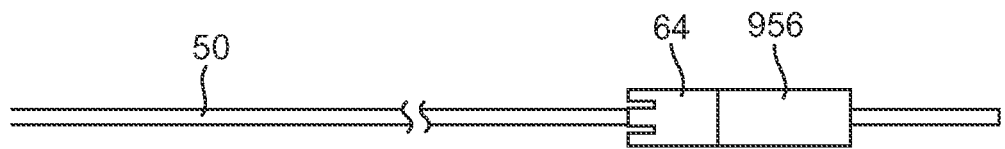
FIGS. 20A, 20B, 20C, 20D, 20E, 20F, 20G, 20H, and 20I illustrate a method for loading a stent in the distal section of the delivery guide according to one embodiment of the invention.

Referring to FIG. 20A, distal seat 64 with extension tube 956 (insulation tubes 959a,b are not shown for simplification) is placed over the central tube or mandrel 50 so that it can rotate about the tube or mandrel 50. A temporary blocker (not shown) (e.g., a tube or drop of epoxy or solder) can be placed on the tube or mandrel 50 distal to extension tube 956 to prevent seat 64 and extension tube 956 from moving distally during assembly. If a distal radiopaque marker is used, it can be placed over extension tube 956. Alternatively, the distal seat can comprise or include radiopaque markers so that an additional marker need not be added.

Figure 20B:
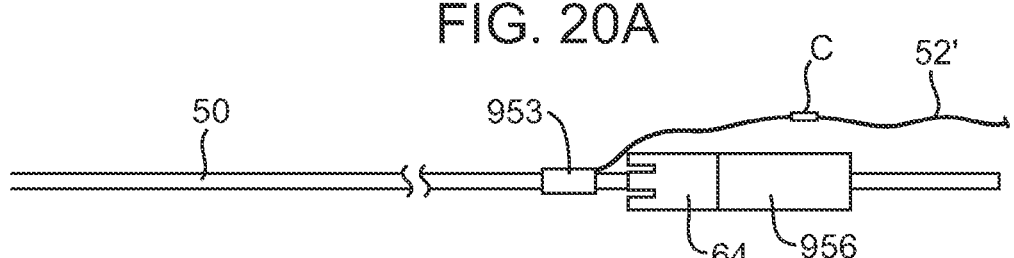

Referring to FIG. 20B, a distal releasable stent restraint mechanism with connector "C" is slid over the proximal end of central tube or mandrel 50 and moved toward seat 64. In the illustrative embodiment, tube assembly 953 with restraint 952, connector "C" and lead 52' extending therefrom is slid over the proximal end of central tube of mandrel 50 toward seat 64. When in the desired location, blocker 954 (FIGS. 18A and 18B) is attached to central tube or mandrel 50 as described above.

Figure 20C:
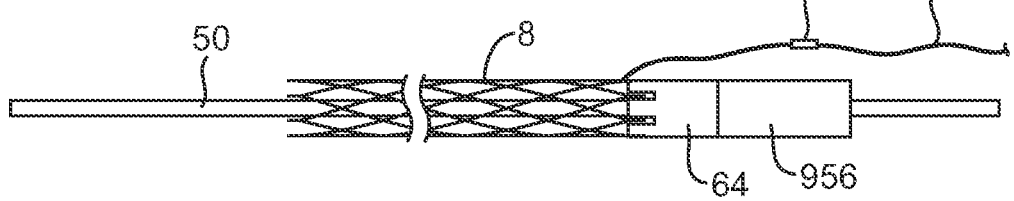

Referring to FIG. 20C, stent 8 is radially compressed and positioned in a plurality of spaced sleeves. Further discussion of stent loading in sleeves can be found in above-referenced U.S. patent application Ser. No. 11/265,999, which published as U.S. Patent Application Publication No. 2007/0100414, and U.S. patent application Ser. No. 11/957,211, which published as U.S. Patent Application Publication No. 2008/0221666, the disclosures of each of these references being incorporated by reference herein. The sleeve retained stent is slid over the proximal end of central tube or mandrel 50 and its distal projections or tabs placed in distal seat 64.

Figure 20D:
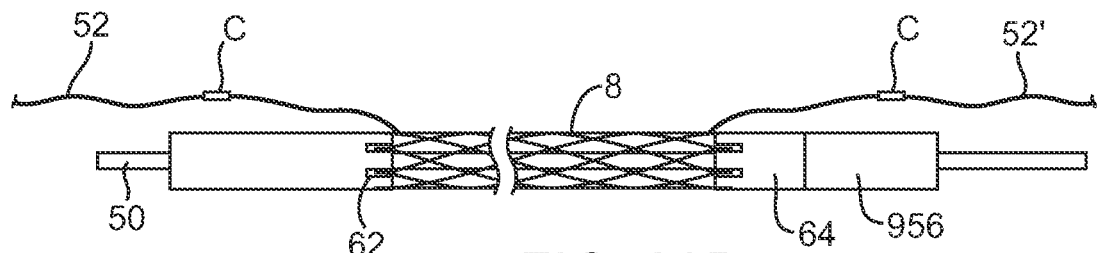

Referring to FIG. 20D, tube 914 (FIG. 13) is loaded on central tube or mandrel 50 and proximal seat 62 is loaded on central tube or mandrel 50. A temporary blocker, e.g., a drop of epoxy or solder (not shown) is placed on central tube or mandrel 50 proximal to the proximal seat 62 to prevent proximal seat 62 from moving proximally during assembly. Then the distal loading sleeve (of the three loading sleeves) is moved distally so it is positioned over the distal seat 64 allowing about one-half to one third of the stent to expand. Then the entire stent is moved distally after which the both ends of proximal seat 62 are soldered to central tube or mandrel 50 to fix seat 62 to central tube 50 after which the temporary blocker is removed. The proximal restraint, which can be in the form of a suture, is secured in tube 914 with epoxy and lead 52 secured to central tube or mandrel 50 as shown in FIG. 5A. Marker band 904 is then mounted as shown in FIG. 5A and secured to center tube 50 with epoxy.

Figure 20E:
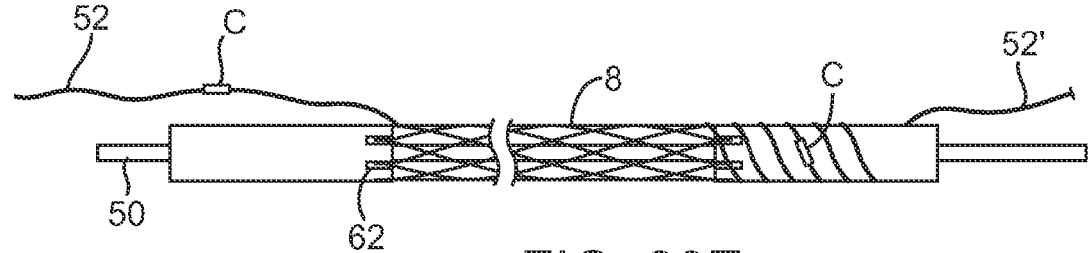
Figure 20F:
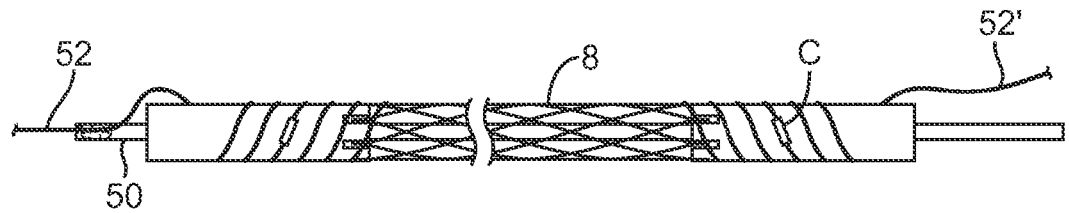

Referring to FIG. 20E, the distal restraint is wrapped around seat 64 and terminates at connector "C". Lead 52', which extends from connector "C", is wrapped around extension tube 956 and epoxied to insulation tube 959b. Then the proximal restraint is wrapped around proximal seat 62 and lead 52 epoxied to central tube or mandrel 50 as shown in FIG. 20F.

Figure 20G:
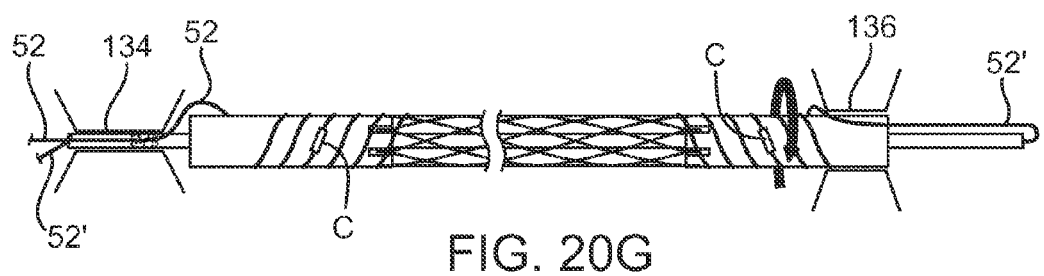

Referring to FIG. 20G, lead 52' is inserted into and passed through central tube or mandrel 50 and clamps 134 and 136 are placed on central tube or mandrel 50 and extension tube 956. Distal clamp 136 is twisted to twist stent 8. Then the distal seat 64, which is secured to extension tube 956, is locked relative to center tube or twist mandrel by joining extension tube 956 to the center tube or twist mandrel 50.

Figure 20H:

Referring to FIG. 20H, the distal clamp is removed and the tip coil 30' is attached as shown in FIG. 18B.

Figure 20I:
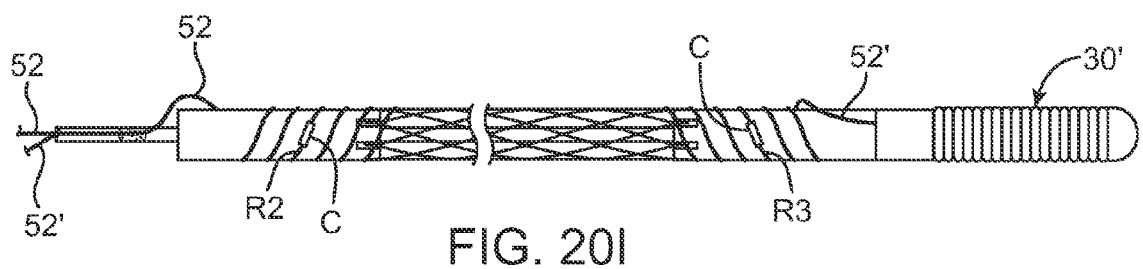

Referring to FIG. 20I, proximal clamp 134 is removed and stent 8 is in torsion.

For stent deployment, power first is provided to sacrificial link "R3." When sacrificial link R3 breaks, the restraint, which is in the form of a wrap or coil, loosens. As a result, the distal end of the stent is released allowing stent 8 to untwist and shorten and the distal end to expand. Power is then provided to sacrificial link "R2." When sacrificial link "R2" is eroded or breaks, restraint wrap 55 loosens and proximal tabs 60b of stent 8 radially expand and become released from delivery guide or guidewire 22.

Power delivery will now be described. In one exemplary embodiment, release of the stent is accomplished by applying a DC voltage to achieve corrosion/erosion of the implant release means. And while adding an AC voltage component for sensing purposes is known (e.g., as described U.S. Pat. No. 5,569,245 to Guglielmi, et al. and U.S. Pat. No. 5,643,254 to Scheldrup, et al.), AC voltage is preferably used herein in a very different manner.

Specifically, it has been appreciated that the use of significant AC component offset by a DC signal can dramatically improve the process of implant delivery through electrolytic corrosion. Not to be bound by a particular theory, but it is thought that efficiency gains are related to controlling blood electrocoagulation and/or having periods of higher peak voltage during the upsweep of the AC signal. The benefits derived from the AC component is especially advantageous in coronary therapy because high frequency (e.g., 10 kHz to 100 kHz or greater) AC power does not affect heart rhythm unless the waveform becomes unstable.

Controlling electro-coagulation is very important for safety reasons (e.g., in avoiding emboli formation that could lead to stroke or other complications) and also to increase the speed of corrosion. Generally speaking, while corroding a positively charged section of metal, the positive charge attracts negatively charged blood cells which coagulate on the surface of the metal. Coagulated blood cells can cover the corroding metal and slow the deployment process. Higher DC levels can be employed to push past this effect, but for safety considerations (especially in the vicinity of the heart) it is desirable to use lower DC voltages. Instead, when an AC signal is employed that drops the trough of the waveform into the negative regime, an opportunity exists to repel the negatively charged blood cells. The resulting decrease or lack of electrocoagulation offers an efficiency increase so that DC voltage can be dropped while maintaining deployment times that are subjectively acceptable to a medical practitioner (e.g., less than about 1 minute or about 30 seconds—even as little as a few seconds).

Power is preferably delivered by a custom battery-powered power supply. Most preferably, a current-control hardware and software driven (vs. software-only driven) power supply is employed. Still, various power/function generators, such as a Fluke model PM 5139 Function Generator, can be employed for experimental purposes. A square wave function is most advantageously employed in order to maximize the time spent at peak and minimum voltage levels, but sinusoidal, saw-tooth, and other variations of these forms can be employed. Still further, frequency modulated waveforms in which more or less time is spent in the positive or negative regimes can be employed.

The power profile applied to the delivery guide can be as described in U.S. patent application Ser. No. 11/265,999, which published under U.S. Patent Application Publication No. 2007/0100414 (the disclosure of each of these references being hereby incorporated herein by reference in its entirety). Specifically, a square wave at about 100 kHz with a 10V peak to peak (10 Vpp) AC component that is offset by a 2.2V DC signal can be employed. The superposition of signals results in a square wave with a 7.2V peak and −3.8V trough. With the addition of an AC profile of at least 4 Vpp, however, the DC component could drop to as low as about 1V to about 1.5V giving a resulting waveform with a peak from 3 to 3.5V and a trough from −1 to −0.5V and still offer an acceptable rate of corrosion. More typically, a square wave at about 100 kHz with a 20V peak to peak (20 Vpp) AC component that is offset by a maximum of 9.0 VDC signal can be employed. The superposition of signals results in a square wave with a maximum of 19V peak and −1.0 trough.

In porcine blood, it was determined that a peak waveform voltage of above 8V begins to cause electrocoagulation, even with trough voltages of −6 to −7V. The level of electrocoagulation varies with the level of the DC component and the size of the piece of metal to be eroded, but usually the peak voltage at the site of the erodible sections should remain below 9V and most often below 8V to avoid appreciable electrocoagulation.

In view of the above, and further for safety reasons—especially in the vicinity of the heart—it may be desirable to maintain the DC component of the power applied at the erodible section(s) between about 1 and about 5V, and more preferably between about 1.75 and about 3V, and possibly most preferably between about 2 and about 3V. The AC waveform employed will generally then be selected to generate a peak at the point of action below about 9V and usually below about 8V, with 7 to 7.5V being typical per the above. Accordingly, the resultant power profile applied at the point of corrosion can have a peak or maximum between about 4 and about 9V, and a minimum of about −0.5 to about −5V. Within this range (and in certain circumstances, outside the range, given situations where some amount of electrocoagulation is acceptable), more effective combinations exist as detailed herein and as can be apparent to those with skill in the art in review of the present disclosure.

A highly effective power profile is shown in FIG. 21A. This figure illustrates the combination of AC component "A" with DC component "B" to yield the power profile "C" applied to the delivery guide. Due to impedance of the system (in this case, modeled at as a stainless steel wire of 6 to 6.5 ft at 0.0012 inch diameter having an impedance of about 2-3 k$\Omega$) a significant drop in the AC voltage is expected, with some drop in the DC voltage as well. As such, the erodible section(s) on the delivery guide can "see" or are subject to a power profile more like that shown in FIG. 21B in which components A' and B' are combined to yield overall power profile C'.

Per the theoretical system shown in FIGS. 21A and 21B, then, power is applied at 15 Vpp at 100 kHz with a DC offset of 3.5 V; the power delivered (to the lead(s) is approximately 6 Vpp with a DC offset of about 2 V. The actual power delivered will vary with details of device construction, material selection, etc.

Irrespective of such variability, an important aspect of the power profile (both as applied and delivered to the erodible material) concerns the manner of its control. Another important aspect concerns the DC component application.

As for the former consideration, as noted above, a current-control power supply is advantageously employed. In a current-controlled implementation, the DC voltage can be allowed to "float" upwards to a maximum of 9.5 V. The AC component remains constant and often yields a net signal in the blood-repulsive regime, but the system can continue to deliver current to produce highly consistent erodible section erosion performance.

Also, in a current-controlled implementation, current can be monitored with precision and offers ease of implementation in a custom system as compared to voltage control hardware. Further, the reaction time of the system can be controlled such that any spike in current persists only for about 1/100,000 of a section. In the kHz range, heart tissue will not respond to any such anomaly. Certain hardware implementations can be preferable over other software implementations where current reaction times can be expected in about 1/200 of a second, or the 50 Hz range—a particularly vulnerable regime for electrical/myocardial interaction. However the control system is implemented, frequencies to which the heart is susceptible should be avoided.

As for DC component application, references to components B and B' in FIGS. 21A and 21B illustrate an advantageous approach. Specifically, DC voltage (hence, power) is increased gradually. By doing so (e.g., over a period of time of about 1 to about 2 seconds), a step function that the heart can react to is avoided. In practice, a shorter ramp-up time can be acceptable (e.g., on the order of 0.10 to about 0.25 or about 0.5 seconds) and longer time frames can be employed (e.g., as much as 5 or 10 seconds).

A ramp-up as shown and described offers additional safety to the system as observed in numerous animal trials. Further, the short delay of 1-2 seconds in reaching full power to drive the electrolytic erosion of the erodible sections is not significantly inconvenient in terms of waiting for system action. Indeed, with a power profile as shown in FIG. 21A, latch erosion times (with a proximal erodible section comprising 0.0078 diameter stainless steel and a distal erodible section comprising 0.0012 stainless steel wire with approximately 0.002 to about 0.005 inches exposed and the remainder insulated) averages only 3 to 15 seconds. It is also noted, that while the wire can be thicker in a rotatable stent release assembly than a wrap-style stent release assembly, the rotatable assembly release times can be the lower of the two due to the load on the restraint wrap exerted by the stent.

Last, it is noted that in instances when release may not occur as desired, as determined by monitoring by control hardware/software, that a "ramp-down" regimen analogous to the "ramp-up" aspect of the power profile can be desirable. Such a feature can be desirable in order to add a further measure of safety to account from device mishandling, etc.

The following table sets forth example power parameters for a stent having a construction as shown in FIG. 4A or 4C and having a compressed delivery outer diameter of about 0.014 inch.

| Parameter | Value R1 (Distal) | R2 (proximal) |
|---|---|---|
| AC voltage | 5-20 V pp 3-nomimal) | |
| AC duty cycle | 50% | |
| AC frequency | 110 kHz | |
| AC ramp up and ramp down time | 0.3 sec | |
| DC Voltage limit | 9.0 V | |
| DC current output for loads between 5 k'Ω and 45 k'Ω | 200 μA | |
| DC ramp up and ramp down time | 0.1-5 sec | |
| AC wave form | Square | |

Any feature described in any one embodiment described herein can be combined with any other feature or features of any of the other embodiments whether preferred or not.

Variations and modifications of the devices and methods disclosed herein will be readily apparent to persons skilled in the art. As such, it should be understood that the foregoing detailed description and the accompanying illustrations, are made for purposes of understanding, and are not intended to limit the scope of the invention, which is defined by the claims appended hereto.

What is claimed is:

1. An implant delivery system comprising:
    an elongated delivery guide having a distal end and a proximal end;
    a self-expanding implant mounted on said elongated delivery guide, said implant having a distal end and a proximal end;
    a first restraint releasably coupling one of the implant ends to said delivery guide;
    a second restraint releasably coupling the other of said implant ends to the delivery guide;
    an electrical conductor adapted to be coupled to a power supply and having an erodible section; and
    an electrically nonconductive member that connects said first restraint to said electrical conductor, wherein the electrically nonconductive member electrically isolates the electrical conductor and the first restraint from one another, wherein the electrically nonconductive member comprises an elongated non-conductive body having a first end and a second end, wherein the first restraint extends distally from the first end and wherein the electrical conductor extends proximally from the second end.

2. The system of claim 1, further including another electrical conductor adapted to be coupled to a power supply and having an erodible section and another electrically nonconductive member connecting said second restraint and said another electrically nonconductive member.

3. The system of claim 1 wherein said nonconductive member comprises a polymer.

4. The system of claim 1 wherein said nonconductive member consists of a polymer.

5. The system of claim 1 wherein said restraint comprises an elongated member wrapped around a portion of said stent.

6. The system of claim 5 wherein said restraint comprises a plurality of elongated members wrapped around a portion of said stent.

7. The system of claim 1 wherein said restraint comprises a suture wrapped around a portion of said stent.

8. The system of claim 7 wherein said restraint comprises a plurality of sutures wrapped around a portion of said stent.

9. The system of claim 1 wherein said restraint comprises a loop that is looped around said delivery guide and wrapped around a portion of said stent.

10. The system of claim 1 wherein said restraint includes wrap portion and a coil portion, said wrap portion being wrapped around a portion of said stent and said coil portion being coupled to said wrap portion and said electrically nonconductive member, said coil portion having a memory set unexpanded relaxed configuration and an expanded configuration, said coil being in said expanded configuration when the erodible joint is not eroded, wherein when said erodible joint is eroded said coil moves toward its unexpanded relaxed configuration and pulls said wrapped portion to an unwrapped configuration.

11. The system of claim 10 wherein said coil comprises shape memory material.

12. The system of claim 1 wherein said self-expanding implant comprises a stent.

13. The system of claim 1 wherein the first restraint is embedded within or connected to the first end and wherein the electrical conductor is embedded within or connected to the second end.

14. The system of claim 13, wherein the elongated nonconductive body comprises a solid cylinder.

15. The system of claim 14, wherein the solid cylinder is formed from adhesive.

16. The system of claim 15, wherein the solid cylinder is covered by an insulating tube.

* * * * *